(12) United States Patent
Patterson et al.

(10) Patent No.: US 8,153,589 B2
(45) Date of Patent: Apr. 10, 2012

(54) JNK3 AS A TARGET FOR THE TREATMENT OF ANGIOGENESIS-RELATED DISEASES

(75) Inventors: Cam Patterson, Chapel Hill, NC (US); Xinchun Pi, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 12/764,356

(22) Filed: Apr. 21, 2010

(65) Prior Publication Data

US 2010/0272712 A1    Oct. 28, 2010

Related U.S. Application Data

(60) Provisional application No. 61/172,951, filed on Apr. 27, 2009.

(51) Int. Cl.
*A61K 31/41*  (2006.01)
*A61K 31/00*  (2006.01)
*A61K 33/00*  (2006.01)

(52) U.S. Cl. ............ 514/13.3; 514/1; 514/406; 424/600

(58) Field of Classification Search .................. None
See application file for complete search history.

(56) References Cited

U.S. PATENT DOCUMENTS

2010/0272712 A1    10/2010    Patterson et al.

OTHER PUBLICATIONS

Benouchan et al. (2005). Anti-angiogenic strategies for cancer therapy (review). Intl. J. Oncology. 27:563-571.*
Shimizu et al. (2005). Antineovascular therapy, a novel antiangiogenic approach. Expert. Opin. Ther. Targets. 9(1):63-76.*
Neri et al. (2005). Tumour vascular targeting. Nature Reviews Cancer. 5:436-446.*
Eskens, F. (2004). Angiogenesis inhibitors in clinical development; where are we now and where are we going? British Journal of Cancer. 90:1-7.*
Askari, A., et al., "Effect of stromal-cell-derived factor 1 on stem-cell homing and tissue regeneration in ischaemic cardiomyopathy," *The Lancet*, 2003, vol. 362, pp. 697-703.
Dias, S., et al., "The Role of CXC Chemokines in the Regulation of Tumor Angiogenesis," *Cancer Investigation*, 2001, vol. 19(7), pp. 732-738.
Horuk, Richard, "Survey Chemokine receptors," *Cytokine and Growth Factor Reviews*, 2001, vol. 12, pp. 313-335.
Mirshahi, F., et al., "SDF-1 Activity on Microvascular Endothelial Cells: Consequences on Angiogenesis in in Vitro and in Vivo Models," *Thrombosis Research*, 2000, vol. 99, pp. 587-594.
Molino, M., et al., "CXCR4 on human endothelial cells can serve as both a mediator of biological responses and as a receptor for HIV-2," *Biochimica et Biophysica Acta*, 2000, vol. 1500, pp. 227-240.
Pourtau, J., et al., "Cyclooxygenase-2 activity is necessary for the angiogenic properties of oncostatin M," *FEBS Letters*, 1999, vol. 459, pp. 453-457.
Stamler, J., et al, "Redox Signaling: Nitrosylation and Related Target Interactions of Nitric Oxide," *Cell*, 1994, vol. 78, pp. 931-936.

* cited by examiner

*Primary Examiner* — Christine J Saoud
*Assistant Examiner* — Jon M Lockard
(74) *Attorney, Agent, or Firm* — Alston & Bird LLP

(57) ABSTRACT

Provided herein are methods for treating a subject having or at risk for an angiogenesis-related disorder. The methods include administering to the subject a therapeutically effective amount of an agent that inhibits JNK3 expression, or a therapeutically effective amount of an agent that inhibits JNK3 activity. Disorders that can be treated by these methods include cancer, rheumatoid arthritis, vascular diseases, and other disorders resulting from excessive angiogenesis. The therapeutic agent may be a compound, small molecule, peptide, antibody, antisense nucleic acid, ribozyme, or the like. Methods of identifying a candidate agent that modulates JNK3 expression are also provided.

5 Claims, 6 Drawing Sheets

JNK3 AS A TARGET FOR THE TREATMENT OF ANGIOGENESIS-RELATED DISEASES

CROSS REFERENCE TO RELATED APPLICATION

This application claims the benefit of U.S. Provisional Application Ser. No. 61/172,951, filed Apr. 27, 2009, the contents of which are herein incorporated by reference in their entirety.

FEDERALLY SPONSORED RESEARCH OR DEVELOPMENT

The research underlying a portion of this invention was supported in part with funds from the National Institute of Health, grant numbers HL 61656, HL 03658, and HL072347. The United States Government has certain rights in the inventions disclosed herein.

REFERENCE TO SEQUENCE LISTING SUBMITTED ELECTRONICALLY

The official copy of the sequence listing is submitted electronically via EFS-Web as an ASCII formatted sequence listing with a file named "388232SEQLIST.txt", created on Apr. 20, 2010, and having a size of 2 kilobytes and is filed concurrently with the specification. The sequence listing contained in this ASCII formatted document is part of the specification and is herein incorporated by reference in its entirety.

FIELD OF THE INVENTION

The present invention is directed to compositions and methods for treating angiogenesis-related disorders by modulating the expression and/or activity of JNK3.

BACKGROUND OF THE INVENTION

The CXC chemokines have recently emerged as key regulators of angiogenesis due to their ability to enhance the migratory capacity of endothelial cells and facilitate the homing of EPCs to ischemic tissues (1, 2). Stromal cell-derived factor-1-α (SDF-1α, also called CXCL12) is one of the most potent proangiogenic CXC chemokines. Both in vivo and in vitro data support a critical role for SDF-1α in angiogenesis. SDF-1α treatment of endothelial cells induces tube-like structure formation and migration (3, 4), and SDF-1α increases tubulogenesis of microvascular endothelial cells via enhanced expression of VEGF and FGF and subsequent endothelial cell migration (5). SDF-1α is required for angiogenesis associated with wound healing under conditions in which SDF-1α expression inversely correlates with oxygen tension (6, 7). Likewise, hypoxia-inducible factor (HIF-1)-induced SDF-1α expression in ischemic tissue increases the adhesion, migration and homing of circulating progenitor cells that express the SDF-1α receptor CXCR4, thereby promoting tissue regeneration (8).

Further evidence that SDF-1α acts as a key regulator of angiogenesis comes from observations that CXCR4, also called Fusin or leukocyte-expressed seven-transmembrane-domain receptor (LESTR), and its co-receptor CXCR7 are required for normal cardiac ventricular septum formation and vascular development (9-14). CXCR4 is selectively expressed in vascular endothelial cells and EPCs (8, 15), and its expression is induced by pro-angiogenic factors such as FGF2 and VEGF (16). Although the critical roles of SDF-1α/CXCR4 in endothelial cell migration are well recognized, relatively little is known about the signal transduction pathways that mediate these effects.

SDF-1α-induced EPC migration is mediated in part through activation of the PI3K/Akt/eNOS signal transduction pathway (17). However, the specific role of NO generated by eNOS in SDF1α-induced neovascularization is still poorly understood and the mechanism by which eNOS regulates SDF-1α-induced endothelial migration is not known. Here we characterize the participation of eNOS in the regulation of SDF-1α-mediated endothelial cell activation.

SUMMARY OF THE INVENTION

The present invention provides methods of treating a subject having or at risk for an angiogenesis-related disorder. The methods include administering to the subject a therapeutically effective amount of an agent that modulates JNK3 expression, or a therapeutically effective amount of an agent that modulates JNK3 activity. Disorders that can be treated by specific inhibitors of JNK3 include, but are not limited to, cancer, rheumatoid arthritis, vascular diseases, macular degeneration, diabetic retinopathy, retinopathy of prematurity, and other disorders resulting from excessive angiogenesis. Disorders that can be treated by specific activators of JNK3 include, but are not limited to, cerebrovascular ischemia, renal ischemia, pulmonary ischemia, limb ischemia, ischemic cardiomyopathy and myocardial ischemia. The therapeutic agent may be a compound, small molecule, peptide, antibody, antisense nucleic acid, ribozyme, or the like.

Also provided are methods of identifying a candidate agent that modulates JNK3 expression. The method includes the steps of incubating an endothelial cell that can express a JNK3 protein with a candidate agent under conditions and for a time sufficient for the cell to express the JNK3 protein when the candidate agent is not present. The expression and/or activity of JNK3 is then measured in the cell in the presence of the agent. The expression and/or activity of JNK3 is also measured in a control cell under the same conditions and for the same time. The amount of JNK3 expression in the cell incubated in the presence of the agent and in the control cell is compared. A difference in JNK3 expression and/or activity indicates that the agent modulates JNK3 expression and/or activity. In an embodiment of this method, the agent decreases JNK3 expression and/or activity, which results in a decrease in angiogenesis. In another embodiment, the agent increases JNK3 expression and/or activity, which results in an increase in angiogenesis.

The invention also includes a method of identifying an agent that modulates the binding of a JNK3 polypeptide to a substrate. The method involves comparing the amount of a JNK3 polypeptide bound to a substrate in the presence and absence of a selected agent. A difference in the amount of binding of a JNK3 polypeptide to the substrate indicates that the selected agent modulates the binding of a JNK3 polypeptide. In an embodiment of this method, the binding of a JNK3 polypeptide to a substrate is decreased. In another embodiment, the binding of JNK3 polypeptide to a substrate is increased.

BRIEF DESCRIPTION OF THE DRAWINGS

FIG. 1. eNOS is activated by SDF-1alpha. A, Western blot analysis of eNOS activity in BAECs treated with 50 ng/ml SDF-1alpha for indicated time periods. B, Western blot analysis of BAECs treated with SDF-1alpha with the indicated dosages for 5 minutes. C, Results of a scratch wound healing assay performed on BAECs pretreated with L-NMMA with or without the addition of 50 ng/ml SDF-1alpha *, P<0.05; compared to control cells without SDF-1alpha. #, P<0.05; compared to control cells with SDF-1alpha. D, Results of the Boyden chamber assay with BAECs pretreated with L-NMMA and stimulated with 50 ng/ml SDF-1alpha.*, P<0.05; compared to control cells without SDF-1alpha. #, P<0.05 compared to control cells with SDF-1alpha. E, Western blot analysis of eNOS protein level in BAECs transfected with eNOS siRNA1, 2, 3 or a mixture of the three. F, Results of a Boyden chamber assay using BAECs transfected with eNOS siRNA or control siRNA and stimulated with 50 ng/ml SDF-1alpha.*, P<0.05; compared to control cells without SDF-1alpha. #, P<0.05 compared to control cells with SDF-1alpha.

Figure 2:
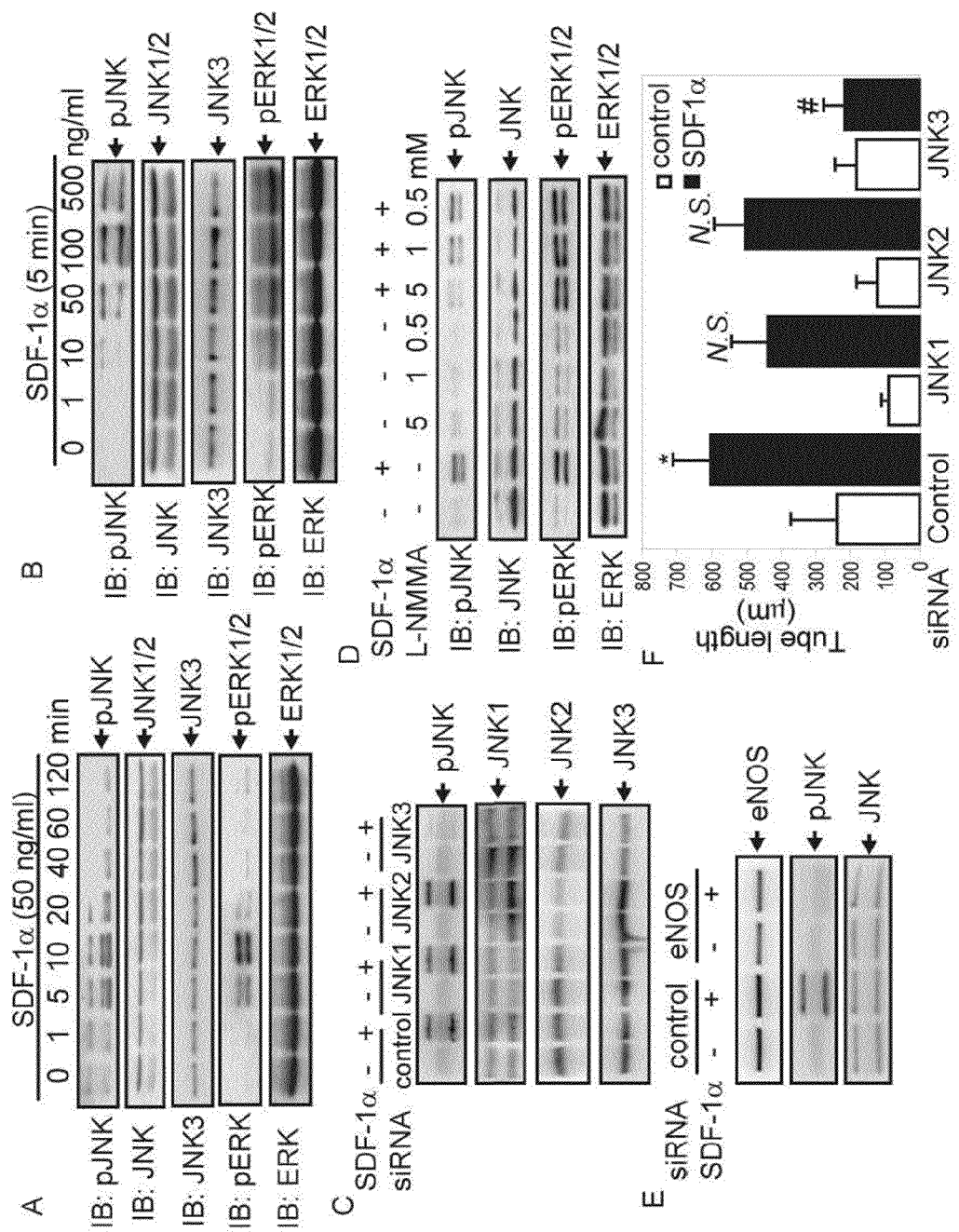

FIG. 2. JNK3 acts as a downstream mediator for eNOS activation induced by SDF-1alpha. A, Western blot analysis of BAECs treated with 50 ng/ml SDF-1alpha for indicated time period. B, Western blot analysis of BAECs treated with SDF-1alpha with the indicated dosages for 5 minutes. C. Western blot analysis of BAECs transfected with siRNAs for JNK1, JNK2 or JNK3 and treated with 50 ng/ml SDF-1alpha for 10 minutes. D, Western blot analysis of BAECs pre-incubated with L-NMMA and then activated with 50 ng/ml SDF-1alpha for 5 minutes. E, Western blot analysis of BAECs transfected with a mixture of eNOS siRNA1-3 and treated with 50 ng/ml SDF-1alpha for 10 minutes. F, Results from a matrigel angiogenesis assay with BAECs transfected with JNK1, JNK2 or JNK3 siRNAs. *, P<0.05; compared to control cells without SDF-1alpha. #, P<0.05; compared to control cells with SDF-1alpha. N.S., not significant.

Figure 3:
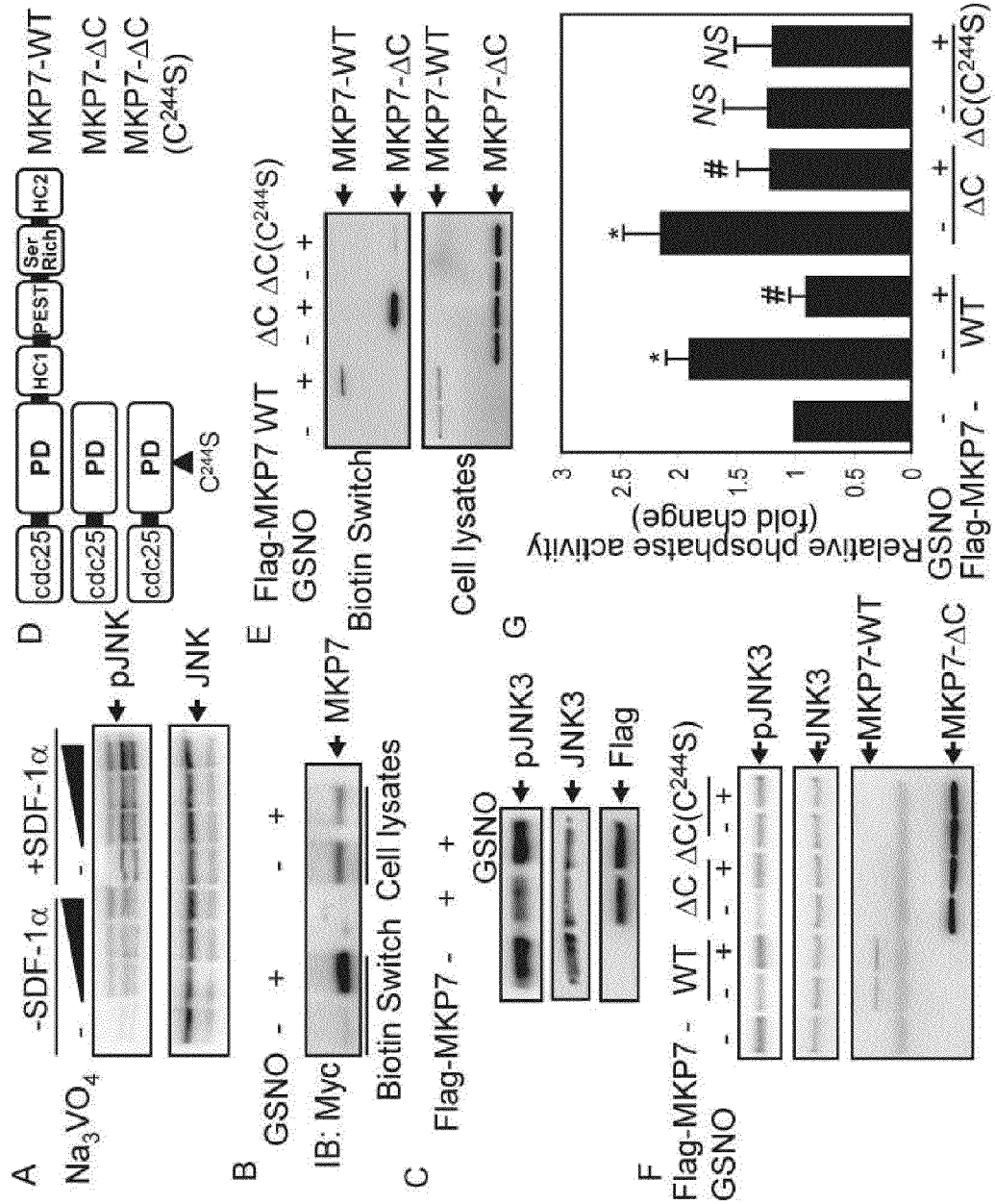

FIG. 3. MKP7 is nitrosylated by nitric oxide. A, Western blot analysis to detect phosphorylated JNK and total JNK protein in BAECs pretreated with $Na_3VO_4$ (10, 100, and 500 µM) and then treated with 50 ng/ml SDF-1alpha for 10 minutes. B, results of a biotin switch assay on HEK293T cells transfected with Myc-MKP7 and treated with the nitric oxide donor-GSNO (500 µM) for 10 minutes at room temperature. C, Results of an in vitro phosphatase assay using active JNK3 protein as the substrate on lysates of HEK293T cells transfected with Myc-MKP7. D, Schematic structure of MKP7 mutant constructs. E, Biotin switch analysis of HEK293T cells transfected with the indicated Flag-tagged MKP7 constructs and then treated with 50 µM GSNO for 10 minutes at room temperature. F, Results of an in vitro phosphatase assay using active JNK3 protein as the substrate on HEK293T cells transfected with flag-tagged MKP7 and then treated with 200 µM GSNO for 10 minutes. G, Quantitative analysis of results from in vitro phosphatase assay of MKP7 based on three independent experiments. *, P<0.05; compared to control cells. #, P<0.05; compared to same cells without GSNO treatment. NS, not significant, compared to control cells or same cells without GSNO treatment respectively.

Figure 4:
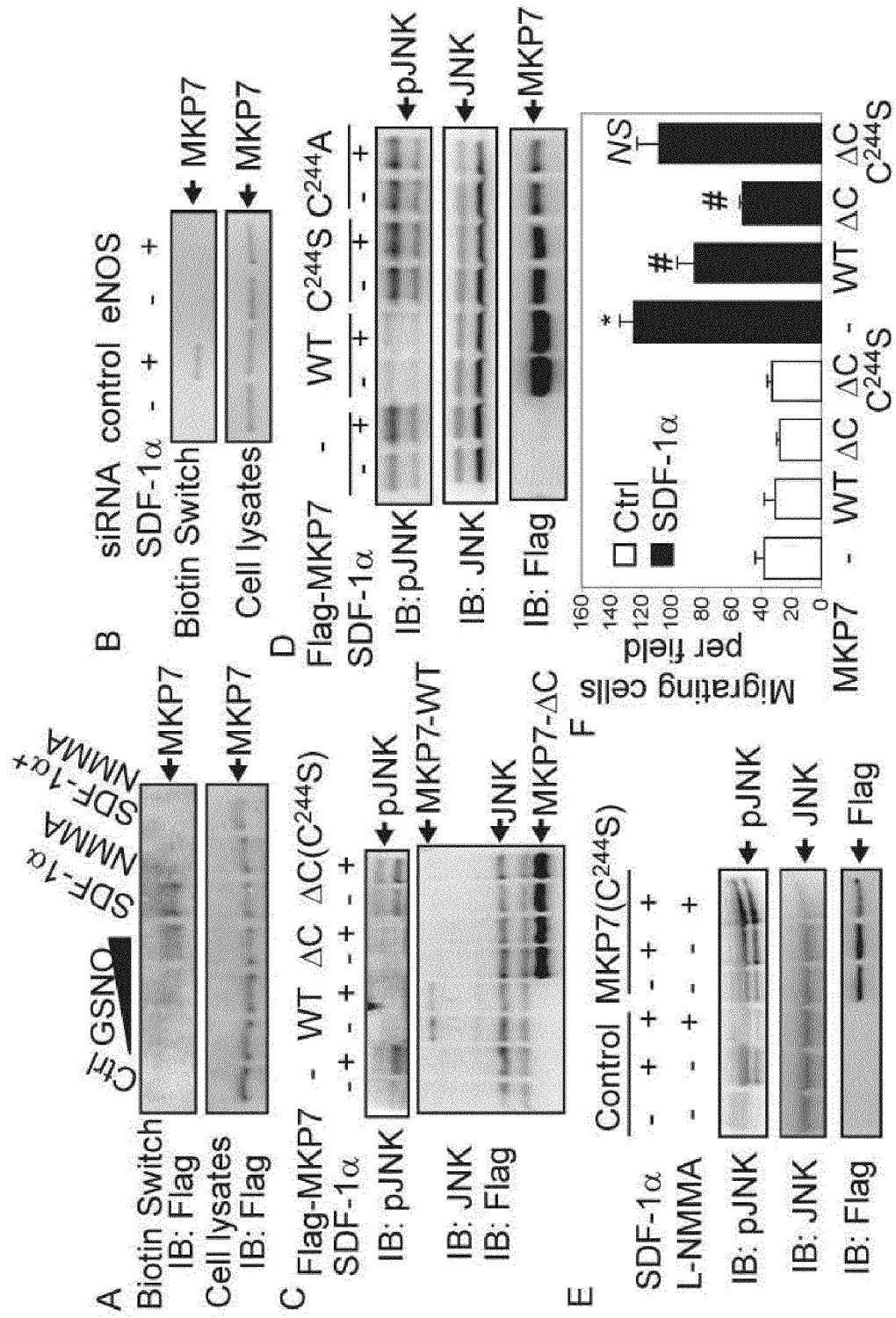

FIG. 4. MKP7 nitrosylated at $Cys^{244}$ is required for SDF-1alpha-induced cell migration. A, Biotin switch analysis of BAECs transfected with flag-tagged MKP7 and incubated with 1 mM L-NMMA followed by treatment with 50 ng/ml SDF-1alpha for 5 minutes. B, Biotin switch analysis of BAECs transfected with a 100 pmol eNOS siRNA mixture and 2 µg Flag-MKP7 and subsequently treated with SDF-1alpha for 5 minutes. C, Western blot analysis of BAECs transfected with flag-tagged MKP7 constructs and activated with 50 ng/ml SDF-1alpha for 5 minutes. JNK activation was determined by the detection of phospho-JNK level in the cell lysates. D, Western blot analysis of BAECs transfected with flag-tagged MKP7 constructs and activated by 50 ng/ml SDF-1alpha for 5 minutes. E, Western blot analysis of BAECs transfected with flag-tagged MKP7-$C^{244}$S or pCMV-empty vector as control, and two days later pretreated with 1 mM L-NMMA for 1 hour and treated with 50 ng/ml SDF-1alpha for 5 minutes. F, Boyden chamber analysis of BAECs transfected with flag-tagged MKP7 constructs using 50 ng/ml SDF-1alpha as the chemoattractant. *, P<0.05; compared to control cells without SDF-1alpha. #, P<0.05; compared to control cells with SDF-1alpha. NS, not significant, compared to control cells with SDF-1alpha.

Figure 5:
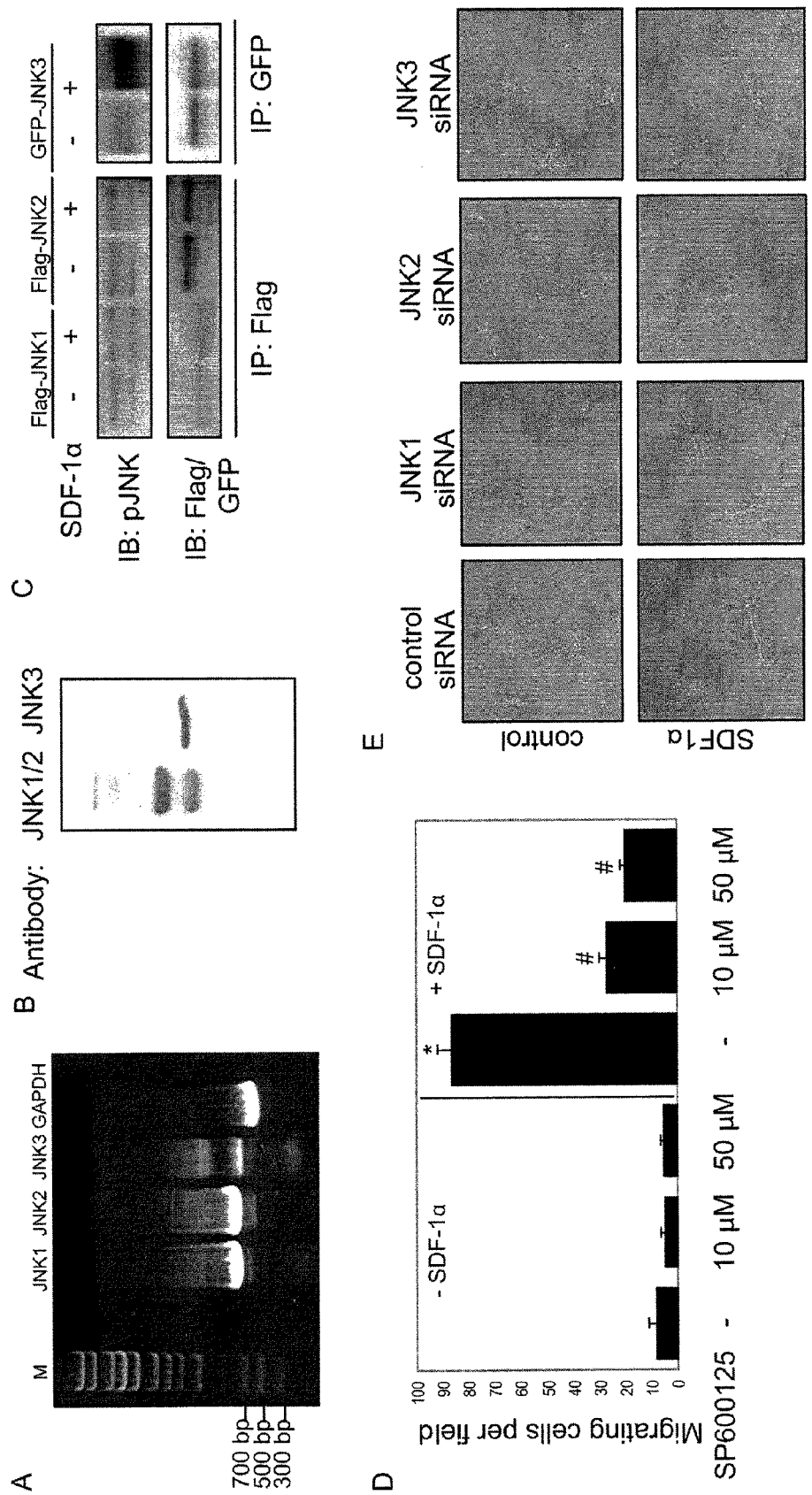

FIG. 5. JNK3 acts as a downstream mediator for eNOS activation induced by SDF-1alpha. A, JNK1, JNK2 and JNK3 mRNA levels in BAECs. B, JNK1, JNK2 and JNK3 expression in BAECs. C, Western blot analysis of BAECs transfected with Flag-JNK1, Flag-JNK2 or GFPJNK3, treated with 50 ng/ml SDF-1alpha for 5 minutes and immunoprecipitated with Flag or GFP antibodies. D, Results of a Boyden chamber assay on BAECs incubated with 10 µM or 50 µM SP600125. 50 ng/ml SDF-1alpha was used as the chemoattractant. *, P<0.05; compared to control cells without SDF-1alpha. #, P<0.05; compared to control cells with SDF-1alpha. E, Images from a Matrigel angiogenesis assay with BAECs transfected with JNK1, JNK2 or JNK3 siRNAs.

Figure 6:
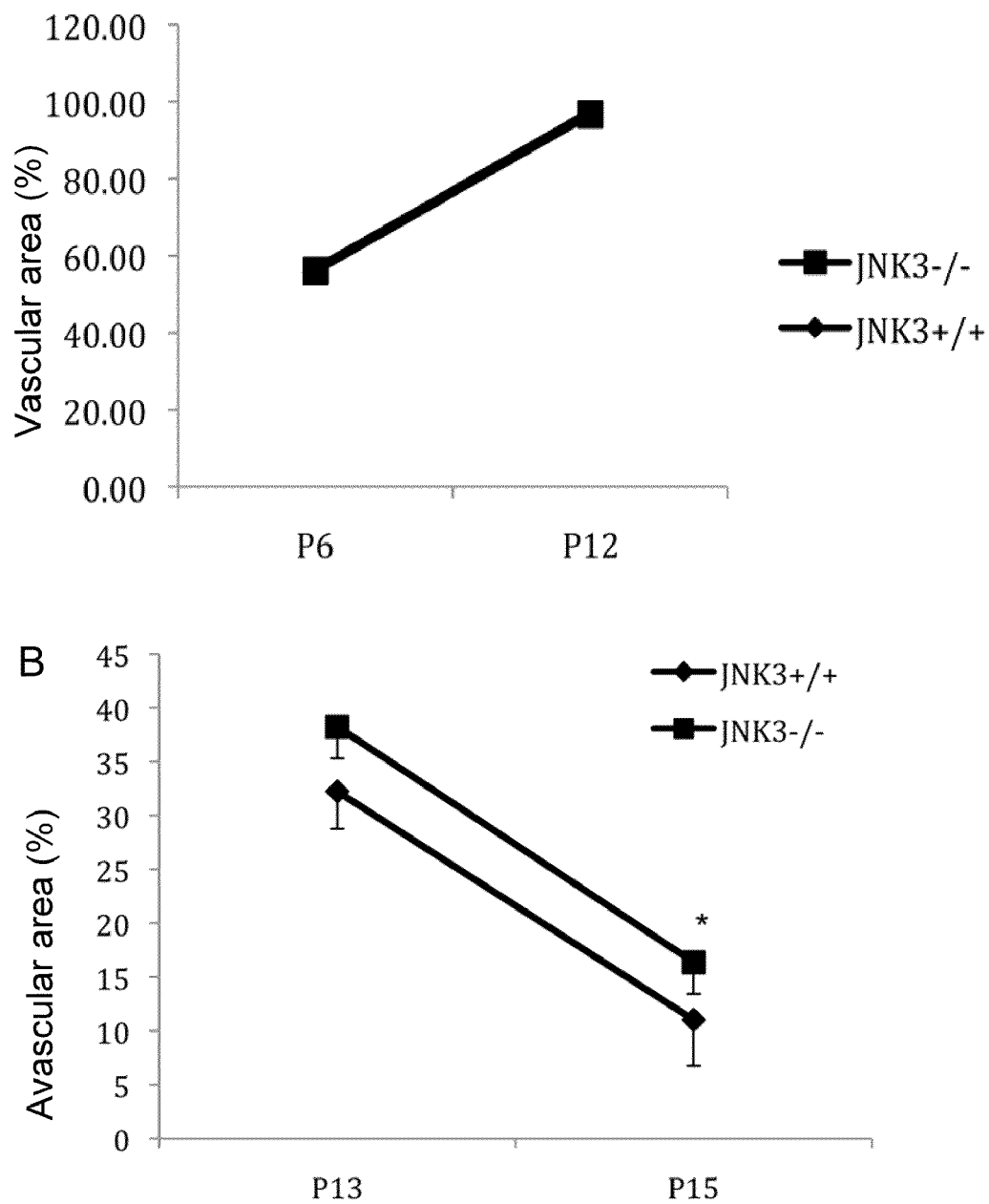

FIG. 6. JNK3 is required for oxygen-induced retinal neovascularization. A. Representative images showing the development of retinal vasculature at postnatal day 6 (P6), as demonstrated with isolectin staining of whole mount retinal vasculature network. B. Quantitative data of retinal vasculature formation in both $JNK3^{+/+}$ and $JNK3^{-/-}$ mice. C. Representative isolectin staining images showing retinal neovascularization following hypoxic injury at P13 and P15. There was markedly decreased retinal vascularization in $JNK3^{-/-}$ mice. *, p<0.05, n=5. D. Graphical data of the comparison of avascularity measured in $JNK3^{+/+}$ and $JNK3^{-/-}$ mice following hypoxic injury.

DETAILED DESCRIPTION OF THE INVENTION

Overview

Angiogenesis, the formation of new blood vessels, is essential for the physiological processes of embryogenesis, tissue growth, and tumorigenesis (Folkman (1995) *Nat Med* 1: 27-31). Under normal physiological conditions, the angiogenic process is controlled by a wide variety of positive and negative regulators, which are composed of growth factors, cytokines, adhesion molecules, and chemokines (Aalinkeel (2004)*Cancer Res* 64: 5311-5321, 2004). It is the balance of these naturally occurring stimulators and inhibitors of angiogenesis that is thought to tightly control the normally quiescent capillary vasculature. When this balance is upset, as in certain disease states, capillary endothelial cells are induced to proliferate, migrate, and differentiate.

Pathological angiogenesis, or the abnormal rapid proliferation of blood vessels, is implicated in over 20 diseases, including cancer, inflammatory diseases, and vascular diseases. Angiogenesis has also been found to be central to the progression of various chronic inflammatory conditions, including diabetic retinopathy, wound healing, and rheumatoid arthritis (Sivakumar (2004) *JAMA* 292: 972-977). These diseases are characterized by chronic inflammation associated with a marked increase in vascular remodeling.

The chemokine stromal cell-derived factor-1alpha (SDF-1alpha) is a pivotal player in angiogenesis by promoting endothelial cell migration as well as endothelial progenitor cell mobilization and homing processes. While not being bound by any particular theory or mechanism, it is believed that c-Jun N-terminal kinase 3 (JNK3) is involved in SDF- 1alpha-mediated endothelial cell migration. JNK (also known as stress-activated protein kinase, or SAPK) is a serine/threonine protein kinase that phosphorylates two residues (Ser-63 and Ser-73) on the $NH_2$-terminal activation domain of c-Jun (Whitmarsh et al., supra; Derijard et al., Cell, 76:1025-1037, 1994; Kyriakis et al., Nature, 369:156-160, 1994). The present invention provides evidence to suggest that JNK3 is activated in endothelial cells via SDF-1alpha-induced activation of eNOS through the phosphatidylinositol 3-kinase (PI3K)/Akt/endothelial nitric oxide (NO) synthase (eNOS) signal pathway. Phosphorylation of ERK, Akt, and eNOS is an important signaling event for angiogenesis (Dong et al. (2001) Cancer Res 61: 5911-5918; Nanki et al. (2004) J Immunol 173: 7010-7016). In the model disclosed herein, SDF-1 alpha activates eNOS, which stimulates production of nitric oxide. Nitric oxide, in turn, nitrosylates and inactivates MKP7 (or DUSP16), which is a JNK3 phosphatase that binds to the JNK3 adaptor protein of β-arrestin2. Nitrosylated MKP7 is unable to prevent phosphorylation of JNK3, thereby leading to JNK3 activation and subsequent endothelial cell migration.

Prior to the present invention, JNK3 was not known to even be expressed in endothelial cells. JNK3 has been previously been predominantly linked to neuronal signaling (18), and thought to play an important role during apoptotic cell death. Therefore, JNK3 has been implicated in various disorders including traumatic brain injury, Alzheimer's disease, Parkinson's disease, and the like. Thus, the present invention provides a novel target modulating angiogenesis.

Provided herein are methods for treating a subject for an angiogenesis-related disorder by inhibiting or activating JNK3 in angiogenesis-associated cells or tissue (e.g., in endothelial cells). As used herein, "treating" is meant reducing, preventing, and/or reversing the symptoms in the individual to which the JNK3 modulator has been administered, as compared to the symptoms of an individual not being treated according to the invention. The terms "inhibit," "inhibition," and "inhibiting" as used herein refer to any decrease (e.g., compared to control) in the expression or function of a target gene product (e.g., JNK3, or a gene product that positively regulates JNK3), including any relative decrement in expression or function up to and including complete abrogation of expression or function of the target gene product. The terms "activate" or "enhance" refer to any increase (e.g., compared to control) in the expression or function of a target gene product (e.g., JNK3, or a gene product that positively regulates JNK3). The term "expression" as used herein in the context of a gene product refers to the biosynthesis of that gene product, including the transcription and/or translation and/or assembly of the gene product. The term "function" refers to the activity if JNK3, e.g., protein kinase activity. The "activity" of JNK3 can also refer to the angiogenic activity of JNK3.

For the purpose of the present invention, an inhibitor is any agent which reduces or blocks the activity of the JNK enzyme. The inhibitory effect may be direct (e.g., the inhibitor directly binds to and/or decreases the expression of JNK3), or indirect (e.g., the inhibitor modulates an upstream regulator of JNK3, such as SDF-1alpha, CXCR4, eNOS, MKP-7, beta-arrestin2, and the like, in a manner that results in a decrease in JNK3 activity and/or expression). Likewise, an activator is any agent which increases the activity of the JNK enzyme. The activator effect may be direct (e.g., the activator directly binds to JNK3 in a manner in which the enzyme activity or stability is enhanced) or indirect (e.g., binds to an upstream regulator of JNK3 in a manner in which the upstream negative regulator is incapable of blocking JNK3 expression and/or activity or in a manner in which an upstream positive regulator increases the expression or activity of JNK3).

In various embodiments, the methods of the invention comprise administering to a subject in need thereof a therapeutically-effective amount of an agent that specifically binds JNK3 and modulates (i.e., activates or inhibits) its expression and/or activity. By "binds specifically" or "specific binding" is intended that the agent binds to JNK3 but not other JNK isoforms (e.g., JNK1 and JNK2). In some embodiments, a peptide that binds specifically to JNK3 binds at least 10%, 20%, 30%, 40%, 50%, 60%, 70%, 80%, 90%, 100%, 200%, 300%, 400%, 500%, or a higher percentage more than the agent binds to an appropriate control such as, for example, JNK1 or JNK2. The term "therapeutic," "therapeutically," and permutations of these terms are used to encompass therapeutic, palliative as well as prophylactic uses. Hence, as used herein, by "treating or alleviating the symptoms" is meant reducing, preventing, and/or reversing the symptoms of the individual to which a JNK3 modulator has been administered, as compared to the symptoms of an individual receiving no such administration. As used herein, "symptom" denotes any sensation or change in bodily function that is experienced by a subject and is associated with a particular angiogenesis-related disease or disorder, i.e., anything that accompanies the disorder and is regarded as an indication of the existence of the disorder. It is recognized and understood that symptoms will vary from disease to disease or condition to condition.

Angiogenesis-Related Diseases

The methods disclosed herein are useful for treating angiogenesis-related diseases or disorders. By "angiogenesis-related diseases or disorders" is intended any pathophysiological condition that depends upon the growth of new blood vessels for development or progression or is the result of a lack of blood vessel growth. Thus, inhibition of JNK3 may result in amelioration of diseases which depend upon blood vessel growth, and activation of JNK3 may result in amelioration of diseases resulting from a lack of blood vessel growth.

Excessive angiogenesis occurs in diseases such as cancer, diabetic blindness, age-related macular degeneration, rheumatoid arthritis, psoriasis, and more than 70 other conditions. In these conditions, new blood vessels feed diseased tissues, destroy normal tissues, and in the case of cancer, the new vessels allow tumor cells to escape into the circulation and lodge in other organs (tumor metastases). Excessive angiogenesis occurs when diseased cells produce abnormal amounts of angiogenic growth factors, overwhelming the effects of natural angiogenesis inhibitors.

Angiogenesis is involved in the formation of new vessels, and is essential for tumor growth and metastases. Antiangiogenic agents have been used to treat metastatic cancer and to prevent or decrease tumor growth. However, many of these therapies are not tolerated due to the toxic side effects of these agents on immune function (reviewed in Mauriz and Gonzalez-Gallego (2008) J. Pharm. Sci. 97(10):4129-54). The present invention provides a particularly beneficial mechanism for controlling angiogenesis by selectively targeting JNK3. Selective modulation of JNK3 may reduce the toxic side effects observed in non-selective JNK modulation and other pro- or antiangiogenic agents.

Cardiovascular disease and its associated maladies, dysfunctions and complications are a principal cause of disability and the chief cause of death in the United States. One factor contributing to cardiovascular disease is atherosclerosis. Atherosclerosis is a disease characterized by the deposition of fatty substances, primarily cholesterol, and subsequent fibrosis in the inner layer of an artery, resulting in plaque deposition on the inner surface of the arterial wall and degeneration. If allowed to progress, atherosclerosis can cause narrowing and obstruction of the lumen of the artery resulting in diminished or occluded blood flow. This can lead to ischemia or infarction of the predominantly affected organ or anatomical region, such as the brain, heart, intestine, or extremities. The use of angiogenesis inhibitors, specifically JNK3 inhibitors, to cut off the blood supply to the plaques may prevent atherosclerosis and its complications, including heart attack, stroke, and peripheral vascular disease.

Angiogenesis also plays a pivotal role in the development of diabetic retinopathy and age-related macular degeneration, both of which are major causes of blindness, as well as retinopathy of prematurity in preterm infants (Wong T. Y., et al. Am. J. Opthalmol. 2006; 141:446-455). As these disorders progress, the blood vessels of the eye not only proliferate excessively, but the new vessels are weak and leaky and prone to hemorrhage. In both macular degeneration and diabetic retinopathy, new abnormal vessels bleed and cause blindness.

JNK3 inhibitors may also have a role in treating endometriosis, which is characterized by the migration of tissue from the lining of the uterus to the ovaries, urethra and other pelvic structures. The migrant tissue waxes and wanes just as the endometrium does during the menstrual cycle. As it grows, it can interfere with ovarian function and become a source of pain. Angiogenesis inhibitors may be able to "starve" the unwanted tissue by robbing it of its rich blood supply.

Other angiogenesis-related diseases and disorders for which JNK3 inhibitors can be used to treat include rheumatoid arthritis, Crohn's disease, psoriasis, uterine fibroids, benign prostatic hypertrophy, preeclampsia, and certain diseases of premature infants.

Diseases which result from insufficient angiogenesis can be treated with activators of JNK3, particularly JNK3-specific activators. Endothelial cells within normal vascular tissues change as they grow older, exhibit reduced angiogenesis and reduced capacity for re-endothelialization. These changes can lead to a diminished capacity for blood vessel formation, a reduction in blood flow to the associated organ or system, and an inability to recover from injuries or diseases that adversely affect blood vessels. Thus, in one embodiment, the present invention may be used to enhance blood vessel formation in arterial occlusive disease, particularly in atherosclerosis. The activators may also be used to enhance blood vessel formation in ischemic tissue, i.e., a tissue having a deficiency in blood as the result of an ischemic disease. Such tissues can include, for example, muscle, brain, kidney and lung. Ischemic diseases include, for example, cerebrovascular ischemia, renal ischemia, pulmonary ischemia, limb ischemia, ischemic cardiomyopathy and myocardial ischemia. Activators of JNK3 can also be used to enhance wound healing.

The angiogenesis-related diseases treated by the present invention are diseases of mammals. The word mammal means any mammal. Some examples of mammals include, for example, pet animals, such as dogs and cats; farm animals, such as pigs, cattle, sheep, and goats; laboratory animals, such as mice and rats; primates, such as monkeys, apes, and chimpanzees; and humans. In some embodiments, humans are preferably treated by the methods of the invention.

Pharmaceutical Compositions

The methods of the present invention comprise treatment of angiogenesis-related diseases or disorders by administering to a subject in need thereof a pharmaceutical composition comprising a therapeutically-effective amount of a JNK3 modulator. The modulator may be a protein, organic or inorganic molecule, carbohydrate, or other compound which may inhibit the activity and/or expression of JNK3. Such agents include pharmaceuticals and candidate pharmaceuticals which are natural products or which are prepared synthetically. Non-limiting examples include polyketides, steroids, the compounds found in the U.S. Pharmacopoeia, and the products of combinatorial chemical synthesis. Candidate pharmaceuticals include molecules for which no function is known, but which have structural similarity to known compounds with one or more known functions. "Polypeptide" refers to any protein or peptide, naturally occurring or synthetic (including fragments, portions, and mutants of a protein or peptide) composed of amino acids linked by peptide (amide) bonds. The amino acids may be naturally occurring or synthetic, including D- and L-forms of amino acids. The modulator may also be an antisense oligonucleotide, a ribozyme, or an antibody capable of binding to and inhibiting the activity of JNK3.

The pharmaceutical composition is administered to supply a desired therapeutic dose to promote a desired therapeutic response of the modulator to the therapeutic area. By "desired therapeutic response" is intended an improvement in the condition or in the symptoms associated with the condition, including the inhibition of angiogenesis.

The compositions of this invention will be formulated in a unit dosage such as a solution, suspension or emulsion, in association with a pharmaceutically acceptable carrier. Such carriers are inherently nontoxic and nontherapeutic. Examples of such carriers are saline, Ringer's solution, dextrose solution, and Hanks' solution. Nonaqueous carriers such as fixed oils and ethyl oleate may also be used. The vehicle may contain minor amounts of additives such as substances that enhance chemical stability, including buffers and preservatives.

Suitable methods of delivery of the pharmaceutical composition include, but are not limited to, gel formulations, viscous solutions, sustained-release formulations, implant delivery systems, such as pumps, and the like. Such delivery systems allow for the controlled and concentrated delivery of the peptide(s) to a therapeutic site. The exact formulation employed will depend on the type of application that is desired.

A pharmaceutically effective amount of a pharmaceutical composition of the invention is administered to a subject. By "pharmaceutically effective amount" is intended an amount that is useful in the treatment of a disease or condition, where treatment can be for a therapeutic purpose as noted herein above. In this manner, a pharmaceutically effective amount of the composition will administer a therapeutically effective dose or amount of the JNK3 modulator to the subject in need of treatment. By "therapeutically effective dose or amount" or "effective amount" is intended an amount of the modulator that, when administered brings about a positive therapeutic response with respect to angiogenesis-related disorders. In some embodiments of the invention, the therapeutically effective dose is in the range from about 0.1 µg/kg to about 100 mg/kg body weight, about 0.001 mg/kg to about 50 mg/kg, about 0.01 mg/kg to about 30 mg/kg, about 0.1 mg/kg to about 25 mg/kg, about 1 mg/kg to about 20 mg/kg, about 3 mg/kg to about 15 mg/kg, about 5 mg/kg to about 12 mg/kg, about 7 mg/kg to about 10 mg/kg or any range of value therein. It is recognized that the method of treatment may comprise a single administration of a therapeutically effective dose or multiple administrations of a therapeutically effective dose.

It is understood that the effective amount may vary depending on the nature of the effect desired, frequency of treatment, any concurrent treatment, the health, weight of the recipient, and the like. See, e.g., Berkow et al., eds., Merck Manual, 16th edition, Merck and Co., Rahway, N.J. (1992); Goodman et al., eds., Goodman and Gilman's The Pharmacological Basis of Therapeutics, 8th edition, Pergamon Press, Inc., Elmsford, N.Y. (1990); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston (1985), Katzung, Basic and Clinical Phamacology, Appleton and Lange, Norwalk, Conn. (1992), which references and references cited therein, are entirely incorporated herein by reference.

The pharmaceutical composition may be contained in a pharmaceutically-acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. The use of such media and agents for delivering cells is well known in the art. Except insofar as any conventional media or agent is incompatible with the cells or polypeptides provided herein, use thereof in the compositions is contemplated. Supplementary active compounds can also be incorporated into the compositions.

A pharmaceutical composition of the invention is formulated to be compatible with its intended route of administration. Examples of routes of administration include intravenous, intraarterial, intracoronary, parenteral, subcutaneous, subdermal, subcutaneous, intraperitoneal, intraventricular infusion, infusion catheter, balloon catheter, bolus injection, direct application to tissue surfaces during surgery, or other convenient routes. The composition can also be injected into an ischemic area of interest, to pharmacologically start the process of blood vessel growth and collateral artery formation.

Solutions or suspensions used for such administration can include other components such as sterile diluents like water for dilution, saline solutions, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The composition can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHORE EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an active agent in the required amount in an appropriate solvent with a selected combination of ingredients, followed by filter sterilization. Generally, dispersions are prepared by incorporating an active agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

It is especially advantageous to formulate the compositions in dosage unit form for ease of administration and uniformity of dosage. Dosage unit form as used herein refers to physically discrete units suited as unitary dosages for the subject to be treated. Each unit can then contain a predetermined quantity of the modulator and other components calculated to produce the desired therapeutic effect in association with the required pharmaceutical carrier.

Implants, Stents and Biomedical Devices

It is recognized that the modulators can be administered to therapeutic sites alone or alternatively may be attached to an acceptable implant, stent, or other biomedical device. In this manner, the implant may be coated with the JNK3 modulator. In some embodiments, the modulators will be attached to the implants. The term "implant" generally refers to a structure that is introduced into a human or animal body to restore a function of a damaged tissue or to provide a new function. An implant device can be created using any biocompatible material.

Gene Therapy

Recently, the feasibility of gene therapy for modulating angiogenesis has been demonstrated (Takeshita, et al., Laboratory Investigation, 75:487-502 (1996); Isner, et al., Lancet, 348:370 (1996); U.S. Ser. No. 08/545,998; Tsurumi et al. (1996) *Circulation* 94(12):3281-90). The JNK3 modulators find use in gene therapy for inhibiting angiogenesis by blocking JNK3 activity, or increasing angiogenesis by increased JNK3 activity, in angiogenesis-associated cells or tissues.

JNK3 modulators can be expressed from vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

In one embodiment, a host cell is genetically modified to contain a stably integrated gene that confers a therapeutic effect by methods available in the art. In one embodiment, the gene that confers a therapeutic effect is a gene that encodes a JNK3-specific modulator.

Antisense Constructs and Therapies

Treatment regimes based on an "antisense" approach involve the design of oligonucleotides (either DNA or RNA) that are complementary to JNK3 mRNAs. JNK3 sequences have been characterized in a variety of mammals. See, for example, GENBANK accession numbers U34819, U34820, U07620, L27128, and L35236. JNK3 also refers to polypeptides that are at least 85% identical to the amino acid sequences listed above, and to the nucleic acids encoding those polypeptides. Examples of these sequences and methods of isolating them are found in Gupta et al., supra, 1996; Kyriakis et al., supra; Martin et al., Brain Res. Mol. Brain. Res., 35:45-57, 1996; and Mohit et al., Neuron, 14:67-78, 1995.

These oligonucleotides bind to the complementary mRNA transcripts and prevent translation. Absolute complementarily, although preferred, is not required. A sequence "complementary" to a portion of an RNA, as referred to herein, is a sequence sufficiently complementary to be able to hybridize with the RNA, forming a stable duplex; in the case of double-stranded antisense nucleic acids, a single strand of the duplex DNA may be tested, or triplex formation may assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence, up to and including the AUG initiation codon, are generally most efficient for inhibiting translation. However, sequences complementary to the 3' untranslated sequences of mRNAs have also been shown to be effective for inhibiting translation (Wagner, Nature, 372:333, 1984). Thus, oligonucleotides complementary to either the 5' or 3' non-translated, non-coding regions of a JNK3 could be used in an antisense approach to inhibit translation of the endogenous human homolog of JNK3 mRNA. Oligonucleotides complementary to the 5' untranslated region of the mRNA should include the complement of the AUG start codon.

While antisense nucleotides complementary to the coding region of a JNK3 gene could be used, those complementary to transcribed untranslated regions are most preferred.

Antisense oligonucleotides complementary to mRNA coding regions are less efficient inhibitors of translation, but could be used in accordance with the invention. Whether designed to hybridize to the 5', 3', or coding region of a JNK3 mRNA, antisense nucleic acids should be at least six nucleotides in length, and are preferably oligonucleotides ranging from 6 to about 50 nucleotides in length. In specific aspects, the oligonucleotide is at least 10 nucleotides, or at least 50 nucleotides in length.

Regardless of the choice of target sequence, in vitro studies are usually performed first to assess the ability of an antisense oligonucleotide to inhibit gene expression. In general, these studies utilize controls that distinguish between antisense gene inhibition and nonspecific biological effects of oligonucleotides. In these studies levels of the target RNA or protein are usually compared with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide, and that the nucleotide sequence of the oligonucleotide differs from the antisense sequence no more than is necessary to prevent specific hybridization to the target sequence.

The oligonucleotides can be DNA or RNA, or chimeric mixtures or derivatives or modified versions thereof, single-stranded or double-stranded. The oligonucleotide can be modified at the base moiety, sugar moiety, or phosphate backbone, for example, to improve stability of the molecule or hybridization. The oligonucleotide may include other appended groups such as peptides (e.g., for targeting host cell receptors in vivo), or agents facilitating transport across the cell membrane (as described, e.g., in Letsinger et al., Proc. Natl. Acad. Sci. USA 86:6553, 1989; Lemaitre et al., Proc. Natl. Acad. Sci. USA 84:648, 1987; PCT Publication No. WO 88/09810) or the blood-brain barrier (see, for example, PCT Publication No. WO 89/10134), or hybridization-triggered cleavage agents (see, for example, Krol et al., BioTechniques 6:958, 1988), or intercalating agents (see, for example, Zon, Pharm. Res. 5:539, 1988). To this end, the oligonucleotide can be conjugated to another molecule, e.g., a peptide, hybridization-triggered cross-linking agent, transport agent, or hybridization-triggered cleavage agent.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The antisense oligonucleotide can also comprise at least one modified sugar moiety selected from the group including, but not limited to, arabinose, 2-fluoroarabinose, xylulose, and hexose.

The antisense oligonucleotide can also include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

The antisense oligonucleotide can include an α-anomeric oligonucleotide. An α-anomeric oligonucleotide forms specific double-stranded hybrids with complementary RNA in which, contrary to the usual β-units, the strands run parallel to each other (Gautier et al., Nucl. Acids. Res. 15:6625, 1987). The oligonucleotide is a 2'-O-methylribonucleotide (Inoue et al., Nucl. Acids Res. 15:6131, 1987), or a chimeric RNA-DNA analog (Inoue et al., FEBS Lett. 215:327, 1987).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (Nucl. Acids Res. 16:3209, 1988), and methylphosphonate oligonucleotides can be prepared by use of controlled pore glass polymer supports (Sarin et al., Proc. Natl. Acad. Sci. USA 85:7448, 1988).

The antisense molecules should be delivered to cells that express JNK3 proteins in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense molecule sufficient to suppress translation of endogenous mRNAs. Therefore, an approach may be used in which a recombinant DNA construct comprises an antisense oligonucleotide placed under the control of a strong pol III or pol II promoter. The use of such a construct to transfect target cells in a subject will result in the transcription of sufficient amounts of single stranded RNAs that will form complementary base pairs with the endogenous JNK3 transcripts and thereby prevent translation of that mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Suitable promoters include, but are not limited to: the SV40 early promoter region (Bernoist et al., Nature 290:304, 1981); the promoter contained in the 3' long terminal repeat of Rous sarcoma virus (Yamamoto et al., Cell 22:787-797, 1988); the herpes thymidine kinase promoter (Wagner et al., Proc. Natl. Acad. Sci. USA 78:1441, 1981); and the regulatory sequences of the metallothionein gene (Brinster et al., Nature 296:39, 1988). Constructs may also be contained on an artificial chromosome (e.g., mammalian artificial chromosome; MAC; Harrington et al., Nature Genet. 15:345-355, 1997).

The production of a JNK3 antisense nucleic acid molecule by any gene therapeutic approach described above results in a cellular level of JNK3 protein that is less than the amount present in an untreated individual.

Ribozymes

Ribozyme molecules designed to catalytically cleave JNK3 mRNAs can also be used to prevent translation of these mRNAs and expression of JNK3 mRNAs (see, e.g., PCT Publication WO 90/11364; Saraver et al., Science 247:1222, 1990). While various ribozymes that cleave mRNA at site-specific recognition sequences can be used to destroy specific mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., Nature 334:585, 1988). Preferably, the ribozyme is engineered so that the cleavage recognition site is located near the 5' end of the JNK3 mRNA, i.e., to increase efficiency and minimize the intracellular accumulation of non-functional mRNA transcripts.

The ribozymes of the present invention also include RNA endoribonucleases (hereinafter "Cech-type ribozymes"), such as the one that occurs naturally in *Tetrahymena Thermophila* (known as the IVS or L-19 IVS RNA), and which has been extensively described by Cech and his collaborators (Zaug et al., Science 224:574, 1984; Zaug et al., Science, 231:470, 1986; Zug et al., Nature 324:429, 1986; PCT Application No. WO 88/04300; and Been et al., Cell 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in JNK3 proteins.

As in the antisense approach, the ribozymes can be composed of modified oligonucleotides (e.g., for improved stability, or targeting), and should be delivered to angiogenesis-associated cells which express a JNK3 gene in vivo, e.g., endothelial cells. A preferred method of delivery involves using a DNA construct "encoding" the ribozyme under the control of a strong constitutive pol III or pol II promoter, so that transfected cells will produce sufficient quantities of the ribozyme to destroy endogenous JNK3 mRNAs and inhibit translation. Because ribozymes, unlike antisense molecules, are catalytic, a lower intracellular concentration is required for efficiency.

For any of the above approaches, the therapeutic JNK3 antisense or ribozyme nucleic acid molecule construct is preferably applied directly to the target area (e.g., the site of excessive angiogenesis), but can also be applied to tissue in the vicinity of the target area or even to a blood vessel supplying the target area.

For gene therapy, antisense, or ribozyme JNK3 expression is directed by any suitable promoter (e.g., the human cytomegalovirus, simian virus 40, or metallothionein promoters), and its production is regulated by any desired mammalian regulatory element.

JNK3 antisense or ribozyme therapy is also accomplished by direct administration of the antisense JNK3 or ribozyme RNA to a target area. This mRNA can be produced and isolated by any standard technique, but is most readily produced by in vitro transcription using an antisense JNK3 DNA under the control of a high efficiency promoter (e.g., the T7 promoter). Administration of antisense JNK3 RNA to target cells is carried out by any of the methods for direct administration of therapeutic agents described herein.

Dosing

A therapeutically-effective agent useful in the methods of the present invention may be administered simultaneously, subsequently or sequentially with one or more other active agents, such as an anti-inflammatory agent e.g. p38 inhibitor, glutamate receptor antagonist, calcium channel antagonist, a chemotherapeutic agent or an antiproliferative agent. For example, for acute treatment, a p38 inhibitor may be administered to a subject prior to administering a JNK3-specific therapeutic agent.

Toxicity and therapeutic efficacy of compounds that modulate JNK3 expression or activity can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Polypeptides or other agents that exhibit large therapeutic indices are preferred. While agents that exhibit toxic side effects may be used, care should be taken to design a delivery system that targets such agents to the site of affected tissue to minimize potential damage to uninfected cells and, thereby, reduce side effects.

The data obtained from the cell culture assays and animal studies can be used in formulating a range of dosage for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (that is, the concentration of the test agent which achieves a half-maximal inhibition of symptoms) as determined in cell culture. Such information can be used to more accurately determine useful doses in humans. Levels in plasma can be measured, for example, by high performance liquid chromatography.

A practitioner will appreciate that the compounds, compositions, and methods described herein are to be used in concomitance with continuous clinical evaluations by a skilled practitioner (physician or veterinarian) to determine subsequent therapy. Hence, following treatment the practitioners will evaluate any improvement in the treatment of the angiogenesis-related disease according to standard methodologies. Such evaluation will aid and inform in evaluating whether to increase, reduce or continue a particular treatment dose, mode of administration, etc.

In various embodiments, the therapeutic agent is administered during a specific phase of disease development or progression. For example, JNK3 inhibitors could be administered at earlier stages of heart disease to help reduce plaque build up, and not at later stages where collateral vessel development could be beneficial to the subject. An early stage of atherosclerosis is defined herein as the stage prior to complete or near complete (i.e., greater than 70%) occlusion of a vessel. Likewise, a JNK3 activator could be administered during the later stages to promote neovascularization rather than during the earlier stages.

Also, JNK3 inhibitors could be used in later stages of cancer development to cause regression in tumor size, or in intermediate stages to block tumor growth altogether. In some embodiments, the JNK3 inhibitor would not be administered prior to tumors reaching a certain size, e.g. at least about 1 cubic mm, at least about 2 cubic mm, at least 3, about 4, about 5, about 6, about 7, about 8 or more cubic mm. It will be recognized that the appropriate criteria, timing, and dosage for JNK3 modulators will be disease-specific, and can be determined by a skilled practitioner.

In yet another embodiment, nontoxic angiogenesis inhibitors can be administered preventively. For example, therapy could be offered to people with a genetically increased risk for cancer (such as women carrying the BRCA1 gene), people with a personal or family history of cancer, and perhaps anyone in whom a simple blood or urine test indicates that a tumor somewhere in the body has "switched on" angiogenesis. Thus, in various embodiments, the JNK3 inhibitor is administered after a positive test for an angiogenesis biomarker.

Non-invasive diagnostic and prognostic urine tests for cancer have been developed that are based on the detection of agents required for angiogenesis, tumor growth, and metastasis (i.e., "biomarkers"). The first of these biomarkers are members of a family of enzymes known as the matrix metalloproteinases (MMPs) (Fernandez et al. (2005) *Clin Cancer Res.* 11(15):5390-5. Another study involved a biomarker called ADAM 12 (Moses, et al. (2004) *J Biol. Chem.* 279(49): 51323-30), which is an indicator of metastatic breast cancer.

Methods of Identifying Modulators of JNK3

Also provided herein are methods for identifying or validating therapeutic agents for antiangiogenic or proangiogenic effects. The methods comprise incubating an endothelial cell that can express a JNK3 protein with a test agent under conditions and for a time sufficient for the cell to express the JNK3 protein when the candidate agent is not present. The expression and/or activity of JNK3 is then measured in the cell in the presence of the agent. The expression and/or activity of JNK3 is also measured in a control cell under the same conditions and for the same time. A "control" cell is a cell that is generally the same, e.g. genotypically and phenotypically, as the cell to which it is being compared (e.g., the cells can be sister cells), but which is not exposed to a test agent. The amount of JNK3 expression in the cell incubated in the presence of the agent and in the control cell is compared. A difference in JNK3 expression and/or activity indicates that the agent modulates JNK3 expression and/or activity. Thus, an increase in JNK3 expression and/or activity indicates that a particular agent is an activator of JNK3 and a decrease in JNK3 expression and/or activity indicates that a particular agent is an inhibitor of JNK3.

As used herein, a "test agent" or "candidate agent" refers to the chemical entities such as, but not limited to, a protein, organic or inorganic molecule, carbohydrate, or other compound for which JNK3 inhibition is tested. A "test agent" of the invention includes pharmaceuticals and candidate pharmaceuticals which are natural products or which are prepared synthetically. Non-limiting examples include polyketides, steroids, the compounds found in the U.S. Pharmacopoeia, and the products of combinatorial chemical synthesis. Candidate pharmaceuticals include molecules for which no function is known, but which have structural similarity to known compounds with one or more known functions. "Polypeptide" refers to any protein or peptide, naturally occurring or synthetic (including fragments, portions, and mutants of a protein or peptide) composed of amino acids linked by peptide (amide) bonds. The amino acids may be naturally occurring or synthetic, including D- and L-forms of amino acids. The test agent may also be an antisense oligonucleotide, a ribozyme, an antibody, or an antibody fragment.

In various embodiments, the test agent is evaluated for its effect on JNK3 activity. In recent years, various technologies for testing protein kinase activities have been developed. Examples of kinase detection technologies available for HTS include the scintillation proximity assay (commercially available from Amersham, Piscataway, N.J.), fluorescent polarization (commercially available from Perkin Elmer, Wellesley, Mass.; Invitrogen, Carlsbad, Calif.; Panvera, Madison, Wis.; and Molecular Devices, Sunnyvale, Calif.), the LANCE™ (Perkin Elmer, Wellesley, MA) assay based on time-resolved fluorescence transfer and time-resolved fluorescence, fluorescence quenching (commercially available from Pierce, Rockford, Ill.), the Z-LYTE™ (Invitrogen/Panvera, Carlsbad, Calif.) assay based on different sensitivity of phosphorylated and non-phosphorylated peptides to proteolytic cleavage, the AlphaScreen™ (Perkin Elmer, Wellesley, Mass.) assay, which is a bead-based non-radioactive luminescent proximity assay, Kinase-Glo™ (Promega, Madison, Wis.), which is a luminescent multi-well assay based on depletion of ATP in a reaction mixture, and an electrocapture assay commercially available from Nanogen (San Diego, Calif.), which is based on change in the charge of a peptide after phosphorylation.

U.S. Pat. No. 6,348,310 and U.S. Pat. No. 6,753,157 disclose a method, a peptide substrate, and kits for quantitating the activity of a selected protein kinase on the peptide substrate. The method comprises conjugating a biotin to a peptide substrate for the kinase, reacting the substrate with a kinase, and detecting a modified substrate. The biotin is used to purify the substrate from the reaction mixture. U.S. Patent Publication No. 20060046277 also describes JNK3-specific assays for detecting the presence and levels of activities of this protein kinase.

The following assays and screens can also be used to identify compounds that are effective modulators of JNK3 activity. The assays and screens can be done by physical selection of molecules from libraries, and computer comparisons of digital models of compounds in molecular libraries and a digital model of the JNK3 active site. The modulators identified in the assays and screens may act by, but are not limited to, binding to JNK3, binding to intracellular proteins that bind to JNK3, compounds that interfere with the interaction between JNK3 and its substrates, compounds that modulate the activity of a JNK3 gene, compounds that prevent phosphorylation of JNK3, or compounds that modulate the expression of a JNK3 gene or a JNK3 protein. Assays can also be used to identify molecules that bind to JNK3 regulatory sequences (e.g., promoter sequences), thus modulating gene expression. See, e.g., Platt, J. Biol. Chem., 269:28558-28562, 1994.

The compounds that can be screened by the methods described herein include, but are not limited to, peptides and other organic compounds (e.g., peptidomimetics) that bind to a JNK3 protein or modulate its activity in any way. Such compounds may include, but are not limited to, peptides; for example, soluble peptides, including but not limited to members of random peptide libraries (see, e.g., Lam et al., Nature 354:82-84, 1991; Houghten et al., Nature 354:84-86, 1991), and combinatorial chemistry-derived molecular libraries made of D- and/or L-amino acids, phosphopeptides (including, but not limited to, members of random or partially degenerate, directed phosphopeptide libraries; see, e.g., Songyang et al., Cell 72:767-778, 1993), and small organic or inorganic molecules. As used herein, the term "small molecule" refers to organic compounds, whether naturally-occurring or artificially created (e.g., via chemical synthesis) that have a relatively low molecular weight and that are not proteins, polypeptides, or nucleic acids. Typically, small molecules have a molecular weight of less than about 1500 g/mol. Also, small molecules typically have multiple carbon-carbon bonds.

Compounds and molecules are screened to identify those that affect expression of a JNK3 gene or some other gene involved in regulating the expression of JNK3 (e.g., by interacting with the regulatory region or transcription factors of a gene). Compounds are also screened to identify those that affect the activity of such proteins (e.g., by inhibiting or enhancing JNK3 activity) or the activity of a molecule involved in the regulation of JNK3.

Computer modeling or searching technologies are used to identify compounds, or identify modified compounds that modulate or are candidates to modulate the expression or activity of a JNK3 protein. For example, compounds likely to interact with the active site of the JNK3 protein are identified.

The active site of JNK3 can be identified using methods known in the art including, for example, analysis of the amino acid sequence of a molecule, and from a study of complexes formed by JNK3 with a native ligand (e.g., ATF2 or c-Jun). Chemical or X-ray crystallographic methods can be used to identify the active site of JNK3 by the location of a bound ligand such as c-Jun or ATF2.

The three-dimensional structure of the active site can be determined. This can be done using known methods, including X-ray crystallography, which can be used to determine a complete molecular structure. Solid or liquid phase NMR can be used to determine certain intra-molecular distances. Other methods of structural analysis can be used to determine partial or complete geometrical structures. Geometric structure can be determined with a JNK3 protein bound to a natural (e.g., c-Jun or ATF2) or artificial ligand which may provide a more accurate active site structure determination.

Computer-based numerical modeling can be used to complete an incomplete or insufficiently accurate structure. Modeling methods that can be used are, for example, parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups are necessary, and can be selected from force fields known in physical chemistry. Information on incomplete or less accurate structures determined as above can be incorporated as constraints on the structures computed by these modeling methods.

Having determined the structure of the active site of a JNK3 protein, either experimentally, by modeling, or by a combination of methods, candidate modulating compounds can be identified by searching databases containing compounds along with information on their molecular structure. The compounds identified in such a search are those that have structures that match the active site structure, fit into the active site, or interact with groups defining the active site. The compounds identified by the search are potential JNK3 modulating compounds.

These methods may also be used to identify improved modulating compounds from an already known modulating compound or ligand. The structure of the known compound is modified and effects are determined using experimental and computer modeling methods as described herein. The altered structure is compared to the active site structure of a JNK3 protein to determine or predict how a particular modification to the ligand or modulating compound will affect its interaction with that protein. Systematic variations in composition, such as by varying side groups, can be evaluated to obtain modified modulating compounds or ligands of preferred specificity or activity.

Given the teachings herein, additional experimental and computer modeling methods useful to identify modulating compounds based on identification of the active sites of a JNK3 protein and related transduction and transcription factors can be developed by those skilled in the art.

Examples of molecular modeling systems are the QUANTA programs, e.g., CHARMm, MCSS/HOOK, and X-LIGAND, (Molecular Simulations, Inc., San Diego, Calif.). QUANTA provides a modeling environment for two dimensional and three dimensional modeling, simulation, and analysis of macromolecules and small organics. Specifically, CHARMm analyzes energy minimization and molecular dynamics functions. MCSS/HOOK characterizes the ability of an active site to bind a ligand using energetics calculated via CHARMm. X-LIGAND fits ligand molecules to electron density patterns of protein-ligand complexes. The program also allows interactive construction, modification, visualization, and analysis of the behavior of molecules with each other.

Articles reviewing computer modeling of compounds interacting with specific proteins can provide additional guidance. For example, see, Rotivinen et al., Acta Pharmaceutical Fennica 97:159-166, 1988; Ripka, New Scientist 54-57 (Jun. 16, 1988); McKinaly and Rossmann, Ann. Rev. Pharmaol. Toxicol 29:111-122, 1989; Perry and Davies, OSAR: Quantitative Structure-Activity. Relationships in Drug Design pp. 189-193 (Alan R. Liss, Inc., 1989); Lewis and Dean, Proc. R. Soc. Lond. 236:125-140, 141-162, 1989; and, regarding a model receptor for nucleic acid components, see Askew et al., Am. J. Chem. Soc. 111:1082-1090. Computer programs designed to screen and depict chemicals are available from companies such as MSI (supra), Allelix, Inc. (Mississauga, Ontario, Canada), and Hypercube, Inc. (Gainesville, Fla.). These applications are largely designed for drugs specific to particular proteins; however, they may be adapted to the design of drugs specific to identified regions of DNA or RNA. Commercial sources of chemical libraries can be used as sources of candidate agents. Such chemical libraries can be obtained from, for example, ArQule, Inc. (Medford, Mass.).

In addition to designing and generating compounds that alter binding, as described above, libraries of known compounds, including natural products, synthetic chemicals, and biologically active materials including peptides, can be screened for compounds that are inhibitors or activators.

Compounds identified by methods described above may be useful, for example, for elaborating the biological function of JNK3 gene products and in treatment of disorders in which JNK3 activity is involved or may contribute. Assays for testing the effectiveness of JNK3 modulating compounds are further described below. In some embodiments, the activity of a test agent is measured by evaluating the effect of the agent on angiogenesis (e.g., by evaluating endothelial cell proliferation, migration, and tubelike structure formation in vivo or in vitro).

In Vitro Screening Assays for Compounds that Bind to JNK3 Proteins and Genes

In vitro systems can be used to identify compounds that can interact (e.g., bind) to JNK3 proteins or genes encoding those proteins. Such compounds may be useful, for example, for modulating the activity of JNK3 polypeptides or nucleic acids, elaborating their biochemistry, or treating disorders related to JNK3 expression (e.g., angiogenesis-related diseases). These compounds may themselves interact with JNK3 or can be used in screens for compounds that interact with JNK3.

Assays to identify compounds that bind to JNK3 proteins involve preparation of a reaction mixture of the protein and the test compound under conditions sufficient to allow the two components to interact and bind, thus forming a complex that can be detected and/or isolated.

Screening assays for molecules that can bind to a JNK3 protein or nucleic acid can be performed using a number of methods. For example, phage display technology is well-known in the art and can be used to identify candidate peptides from a library of diverse peptides. Phage display describes a selection technique in which a library of variants of a peptide or protein is expressed on the outside of a phage virion, while the genetic material encoding each variant resides on the inside (Sidhu et al. (2003) Chembiochem, 4:14-25; Ferrer et al. (1999) J. Pept. Res., 54:32-42; and, BouHamdan et al. (1998) J. Biol. Chem. 273:8009-8016). This creates a physical linkage between each variant protein sequence and the DNA encoding it, which allows rapid partitioning based on binding affinity to a given target molecule (antibodies, enzymes, cell-surface receptors, etc.) by an in vitro selection process called "panning" or "biopanning" (Whaley et al. (2000) Nature 405:665-668). Panning methods can include, for example, solution phase screening, solid phase screening, or cell-based screening.

Thus, a JNK3 protein, peptide, or fusion protein can be immobilized onto a solid phase, reacted with the test compound, and complexes detected by direct or indirect labeling of the test compound. Alternatively, the test compound can be immobilized, reacted with JNK3 polypeptide, and any complexes detected. Microtiter plates can be used as the solid phase and the immobilized component anchored by covalent or noncovalent interactions. Non-covalent attachment may be achieved by coating the solid phase with a solution containing the molecule, and drying. Alternatively, an antibody specific for JNK3 is used to anchor the molecule to the solid surface. Such surfaces may be prepared in advance of use, and stored. JNK3 antibodies can be produced using conventional methods such as those described in Coligan et al. (Current Protocols in Immunology, John Wiley & Sons, Inc., 1994, see Volume 1, chapter 2).

Alternatively, a reaction can be conducted in a liquid phase, the reaction products separated from unreacted components, and complexes detected (e.g., using an immobilized antibody specific for a JNK3 protein).

Cell-based assays can be used to identify compounds that interact with JNK3 proteins. Cell lines that naturally express such proteins or have been genetically engineered to not contain the test compound can be used to determine whether the test compound is an inhibitor or activator of JNK3 activity.

Modulators of JNK3 expression that act on the JNK3 promoter can be identified using a chimeric gene in which genomic sequences including the JNK3 promoter are fused to a reporter, for example firefly luciferase. Cultured cells (including neurons) transformed with this DNA are screened for the expression of luciferase activity. Compounds that inhibit or enhance luciferase activity in this high throughput assay can be confirmed by direct measurement of the endogenous JNK3 protein (by Western blotting) and JNK3 mRNA (by Northern blotting) using methods known in the art (for example, see Ausubel et al., Current Protocols in Molecular Biology, John Wiley & Sons, 1994).

Candidate compounds can be tested further in cell or tissue cultures as well as animal models. For example, cells expressing JNK3 are incubated with a test compound. Lysates are prepared from treated and untreated cells and Western blotted according to known methods. The blots are probed with antibodies specific for JNK3. An increase or a decrease in the amount of JNK3 expression in cultures treated with the test compound compared to untreated controls indicates that the test compound is a candidate for a drug to treat disorders associated with JNK3 expression.

Assays for Compounds that Interfere with JNK3/JNK3 Substrate Interactions

Molecules that disrupt or enhance the interaction between JNK3 and its substrates can be identified using assays that detect protein-protein interactions. For example, the yeast two-hybrid method detects protein interactions in vivo. However, an in vitro assay is preferable because candidate molecules may not be permeable to the yeast cell wall. An example of an in vitro assay for such test molecules that disrupt or enhance the interaction between JNK3 and a substrate includes the use of immobilized JNK3 or immobilized substrate (e.g., c-Jun) and incubation of the immobilized component with cell lysates or purified proteins in the presence and absence of a test molecule. In general, the test molecule is tested over a range of a 100 fold molar excess over the most abundant component (e.g., the component immobilized or in solution). If the test molecule is predicted to interact with the immobilized component of the assay, then it can be pre-incubated with that component before adding the cell lysate or purified protein. After washing away unbound material, the bound proteins are detected with antibodies (e.g., ELISA or Western blot) or through the use of labeled proteins (e.g. radioactive or fluorescent) using methods known in the art. Test molecules that decrease the amount of substrate bound to JNK3 are thus identified as molecules that interfere with JNK3/JNK3 substrate interactions. Test molecules that increase the amount of substrate bound to JNK3 are identified as molecules that enhance the JNK3/JNK3 substrate interactions.

Assays for Compounds that Modulate the Effects of JNK3 In Vivo

Compounds identified as above, or other candidate agents that inhibit or enhance JNK3 activity in vitro may be useful for treating disorders involving JNK3 activity. These compounds can be tested in in vivo assays, for example, in animal models of disorders involving JNK3 activity. For example, test compounds predicted to inhibit or enhance JNK3 activity can be administered to animals that serve as models for the various disease paradigms. Treated animals are then assayed for modulation of JNK3 activity. Such assays may be indirect or inferential, for example, improved health or survival of the animal indicates the efficacy of a test compound. Assays can also be direct, for example, a change in JNK3 or c-Jun expression can be measured by Northern analysis of tissue removed from an animal treated with a test compound. A decrease in the amount of JNK3 mRNA present in the sample from treated animals compared to untreated controls indicates that the test compound is inhibiting JNK3 expression, whereas an increase in the amount of JNK3 mRNA indicates that the test compound is enhancing JNK3 expression. A decrease or an increase in the amount of c-Jun indicates that the test compound is inhibiting or enhancing, respectively, JNK3 expression or activity.

Knockout animals can be used to identify and screen compounds for participation in an angiogenesis-related disease or disorder. For example, JNK3 knockout mice may be used for the study of diabetic retinopathy by observing physiological and pathological retinal vessel formation.

The following examples are offered by way of illustration and not by way of limitation.

EXPERIMENTAL

Example 1

Materials and Methods
siRNA Design and Transient Transfection siRNAs for bovine eNOS, JNK1, JNK2 and JNK3 were designed with BLOCK-iT™ RNAi designer (www.invitrogen.com). eNOS siRNA1 sequence is CGGUGAAGAUCU-CUGCCU CACUCAU (SEQ ID NO:1), eNOS siRNA2 sequence is UGUUGCUGGACUCCUUUCUCUUCCG (SEQ ID NO:2), eNOS siRNA3 sequence is UACGUAUACGGCUUGUCACCUCCUG (SEQ ID NO:3). JNK1 siRNA sequence is AUAACAAAUCCCUUGC-CUGACUGGC (SEQ ID NO:4). JNK2 siRNA sequence is AGUUGAGUCU GCCACUUGUACACUG (SEQ ID NO:5). JNK3 siRNA sequence is a mixture of a) GAUAUAUGG UCUGUGGGAUGCAUUA (SEQ ID NO:6); b) CACUGGAGGAGUUCCAAGAUGUUUA (SEQ ID NO:7); c) UAGCAUCUUUGACAGCAAGUCUCUG (SEQ ID NO:8). The control siRNA sequence is CGGGAAC-UACAAGACA CGUGCUGAA (SEQ ID NO:9). The transfection of siRNA into BAECs was performed with Nucleofector electroporation system following the manufacturer's protocol for HUVEC (Amaxa, Gaithersburg, Md.). After Cells were confluent for 2 days, BAECs were trypsinized and spun down. $1 \times 10_6$ cells were reconstituted with 100 [1 room temperature Nucleofector solution and mixed with 100 pmol siRNA. The cell/DNA suspension was then transferred into cuvettes and the electroporation was performed with A034 program using the Nucleofector electroporation system. The efficiency of transfection was evaluated with pmaxGFP expression and siGlo fluorescence.

Immunoprecipitation and Western Blotting Analysis

Cells were harvested in lysis buffer (1% Triton X-100, 50 mM Tris, pH 7.4, 150 mM NaCl, 1 mM $Na_3VO4$ and 0.1% protease inhibitor tablet; Roche) and clarified by centrifugation at 16,000 g. Equal amounts of proteins were incubated with a specific antibody overnight at 4° C. with gentle rotation. Protein A/G Plus-agarose beads (Santa Cruz Biotechnology, Santa Cruz, Calif.) were used to pull down the antibody complexes. Afterward, beads were washed with lysis buffer, and immune complexes were separated by SDS-PAGE. Total cell lysates were separated by SDS-PAGE and transferred to nitrocellulose membranes.

Biotin Switch Assay

Experiments were performed following the methods previously described by Dr. Stamler's laboratory (39). Cell lysates containing Flag or Myc-tagged MKP7 protein were treated with the indicated concentrations of GSNO followed by the addition of 2 volumes of HEN buffer and freshly prepared S-methyl methanethiosulfonate (10% v/v in N,N-dimethylformamide) and SDS (25% v/v) to final concentrations of 0.1 and 2.5%, respectively. Following frequent vortexing at 50° C. for 1 hour, proteins were precipitated with 3 volumes of acetone at −20° C. for 30 min. The proteins were recovered by centrifugation at 5,000×g for 5 min, followed by gentle rinsing of the pellet with 3×1 ml acetone. The pellets were then resuspended in 240 µl of HEN buffer containing 1% SDS. The resuspended protein was precipitated, rinsed and resuspended once more. For labeling, the blocked samples were mixed with 0.1 volume of biotin-HPDP (2.5 mg/ml in $Me_2SO$) and 0.1 volume of HEN (control) or freshly prepared sodium Ascorbic acid in HEN buffer. Labeling reactions were performed in the dark at room temperature for 1 h unless otherwise indicated. To detect an MKP7 SNO protein from cells or lysates, the labeling reaction was acetone-precipitated as previously described. The washed pellet was resuspended in 250 µl of HEN/10 (HEN diluted 10-fold into $H_2O$) containing 1% SDS, followed by addition of 750 µl of neutralization buffer (25 mM HEPES, 100 mM NaCl, 1 mM ETDA, 1% Triton X-100, pH 7.5). This material was incubated overnight at 4° C. with 40 µl of streptavidin-agarose beads. The beads were washed with 3×1 ml of wash buffer (neutralization buffer+500 mM NaCl) and 2×1 ml of neutralization buffer. The dried beads were eluted with 50 µl of HEN/10+1%-mercaptoethanol. The eluted mixture was then analyzed by SDS-PAGE, followed by immunoblotting with anti-Flag-HRP (1:5000) or antibodies.

In Vitro Phosphatase Assay

Flag-MKP7 protein was prepared from the cells transfected with Flag-MKP7 by immunoprecipitation using Flag beads (Sigma). The precipitate was washed twice with lysis buffer containing high salt (1 M NaCl) followed by 2 washes with the reaction buffer. In vitro phosphatase reactions were carried out at 37° C. for 1 hour in I.V.P.A buffer (20 mM Tris⊕HCl, pH7.0, 0.1 mM MgCl$_2$, 1 mM MnCl$_2$, 1 [g/[1 BSA, 1 mM DTT in reduced samples) with 25 ng active JNK3 purified protein (Upstate). The reaction was stopped by the addition of 2× loading buffer followed by western blotting analysis with phospho-specific JNK and JNK antibodies.

Boyden Chamber Assay

Boyden chamber assays were performed as previously described (40, 41) using a 48-well chamber apparatus (NeuroProbe, Cabin John, Md.). The lower chambers of the apparatus were filled with DMEM with or without SDF-1alpha and then covered with the collagen-coated filter and the upper chambers. Cells pretreated with or without the indicated inhibitors were then added to the upper chambers. After incubating for 6 h at 37° C., cells present on the lower surface were fixed, stained and identified with the 40× objective lens on a Nikon Eclipse TS 100 inverted microscope.

Wound Healing Assay

For detection of cell migration, a wound healing assay was performed as previously described (40). BAECs were grown on 35 mm wells, the monolayer was scratched with a sterile disposable rubber policeman and the edge labeled with a traced line. After injury, the cells were gently washed with normal media without serum. EC migration from the edge of the injured monolayer was quantified by measuring the area between the wound edges before and the recovered area after injury using light microscopy (Eclipse TS100, 4× objective, Nikon) and the computer program ImageJ.

In Vitro Matrigel Angiogenesis Assay

Endothelial cell tube formation was analyzed with the Matrigel-based tube formation assay (40, 41). Chilled 24-well plates were coated with growth factor-reduced Matrigel (Becton Dickinson, San Jose, Calif.) that was polymerized at 37° C. for 30 min. BAECs were transfected with siRNA constructs with the Amaxa Nucleofector electroporation reagent. Three days later, cells were trypsinized, and plated at equal numbers into each Matrigel-coated well. After 18 hours of incubation in the absence or presence of SDF-1alpha, the formation of tubes was photographed (Eclipse, 10× objective, TS100Nikon). Images were quantified with ImageJ.

Results eNOS is Activated by SDF-1α and is Required for Endothelial Cell Migration Induced by SDF-1α

SDF-1α-induced EPC migration is blocked by eNOS and PI3K inhibitors, suggesting that the PI3K/Akt/eNOS signaling axis is required for SDF-1α-dependent progenitor cell activation (17). However, the exact roles of eNOS and nitric oxide in the regulation of SDF-1α-mediated migration in mature endothelial cells are not known. To examine this we first asked the following questions: Does the addition of SDF-1α to mature endothelial cell cultures result in eNOS activation? And, if so, does eNOS play a role in the SDF-1α-induced migration of endothelial cells?

Figure 1:
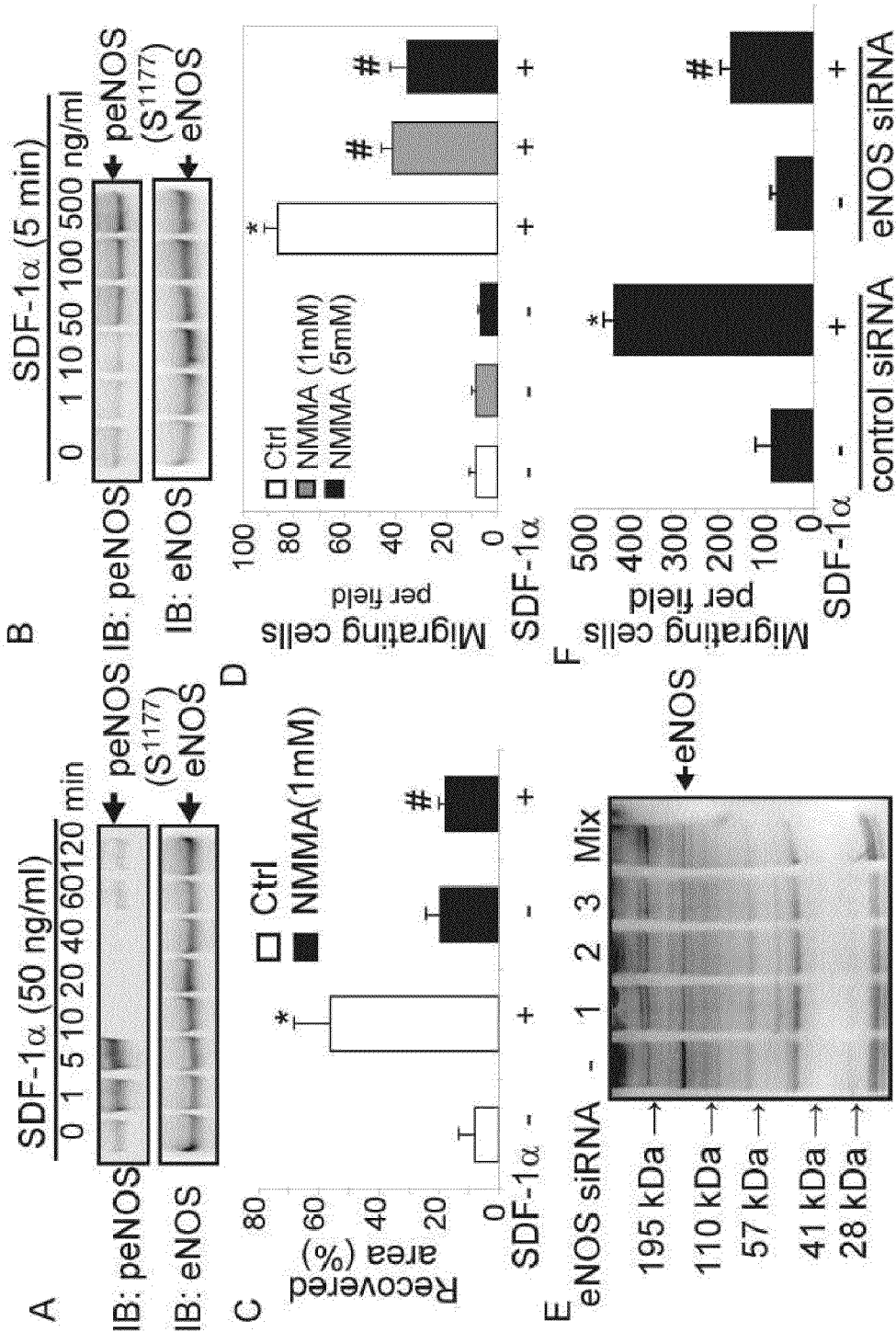

The degree of SDF-1α-induced activation of eNOS was examined in bovine aortic endothelial cells (BAECs) by monitoring phosphorylation of the Ser 1177 activation site in eNOS. Our results demonstrated that eNOS was phosphorylated by SDF-1α in a time- and dose-dependent manner. Phosphorylation of Ser 1177 peaked at 5 minutes after SDF-1α stimulation (FIG. 1A), and increased in a dose-dependent fashion over a SDF-1α concentration range of 50 ng/ml to 500 ng/ml (FIG. 1B), which approximates physiologically relevant SDF-1α concentrations.

To determine whether eNOS activation is required for SDF-1α-mediated endothelial cell migration, we performed scratch-wound healing and Boyden chamber migration assays in the presence of the NOS-specific inhibitor L-NMMA (19). Confluent BAECs were pretreated for one hour with 1 mM or 5 mM L-NMMA or vehicle prior to each assay. In the wound healing assay, SDF-1α increased BAEC migration towards the wounded area from 8.09±5.42% to 56.0±12.0%, whereas L-NMMA-pretreatment inhibited cell migration (from 56.0±12.0% to 17.7±2.4%, FIG. 1C) and significantly decreased wound recovery. Similarly, cell migration in Boyden chambers was induced by SDF-1α (from 8±3 to 86±5 cells per field), but this increase in migration was inhibited by the pre-incubation of BAECs with L-NMMA (FIG. 1D). The involvement of eNOS in SDF-1α-induced endothelial cell migration was confirmed by treatment of cells with siRNAs specific for eNOS. Endothelial cells were transfected with 1 of 3 different bovine eNOS-specific siRNAs, or mixture of all three, and 72 hours later cell lysates were examined by western blot analysis for levels of eNOS protein. Each separate siRNA entity as well as the mixture of all three were found to be similarly effective at suppressing expression of endogenous eNOS in BAECs (FIG. 1E). Likewise, transfection of cells with eNOS-specific siRNA resulted in a significant decrease in migration of cells in response to SDF-1α treatment (FIG. 1F). Therefore, inhibiting eNOS activity either by siRNA or a protein-specific inhibitor is significantly detrimental to SDF-1α-induced endothelial cell migration, indicating that eNOS is activated downstream of SDF-1α in mature endothelial cells and that this activation is required for SDF-1α-stimulated endothelial cell migration.

JNK3, but not JNK1 or JNK2, is Activated by SDF-1α

Mitogen-activated protein kinases (MAPKs), including ERK1/2 and p38, have been reported to enhance angiogenesis (20, 21). However, the role of JNK in angiogenesis remains controversial, with studies showing both positive and negative outcomes of JNK activation. In order to determine which MAPKs are involved in SDF-1α-induced endothelial cell migration, we screened the activities and expression levels of ERK1/2, p38 and JNK following treatment of BAECs with SDF-1α. SDF-1α (50 ng/ml) potently induced JNK and ERK1/2 activities in BAECs (FIG. 2A; note that multiple bands in JNK blots represent splice variants of JNK); however, p38 was not significantly activated by SDF-1α (data not shown). SDF-1α activated both JNK and ERK1/2 in a dose-dependent manner (FIG. 2B). When comparing the time course of SDF-1α-induced activation of JNK and ERK1/2 to that of eNOS, the peak of their activation lagged behind eNOS (compare FIG. 1A with FIG. 2A), suggesting that JNK and ERK1/2 may act downstream of eNOS to transduce the migratory events induced by SDF-1α in endothelial cells. Protein and mRNA for all three JNK isoforms, JNK1, JNK2 and JNK3, can be found in BAECs (FIGS. 5, A&B). In order to determine which JNK protein(s) was activated by SDF-1α in these cells we used a previously described assay (22). Exogenous JNK1, JNK2 and JNK3 proteins containing Flag or GFP-epitopes were transiently expressed in BAECs and their activities were determined via western blotting with a phospho-JNK antibody following SDF-1α treatment. Interestingly, only phosphorylation of JNK3 (but not JNK1 or JNK2) was increased after treatment of endothelial cells with SDF-1α (FIG. 5, C). To confirm the finding that JNK3 is the only JNK entity activated by SDF-1α, we transfected cells with siRNAs for each of the JNK proteins and then tested the effect of each siRNA for the ability to suppress SDF-1α-induced JNK activation. SDF-1α significantly enhanced JNK phosphorylation in the cells transfected with control, JNK1 and JNK2 siRNAs (FIG. 2C). However, the increase of JNK phosphorylation was completely abrogated in the cells transfected with JNK3 siRNA. These results suggest that different JNK isoforms might have different cellular functions in endothelial cells since they are being differentially regulated under these conditions, with JNK3 specifically mediating effects downstream of SDF-1α signaling. Because JNK3 was the only SDF-1α-activated JNK in endothelial cells in our studies (FIG. 2C & FIG. 5, C), we consider the phospho-JNK signals in western blots with anti-phospho-JNK antibody as the signals for activated JNK3.

JNK3 Acts as a Downstream Mediator of SDF-1α-Induced eNOS Activation

Nitric oxide produced by eNOS activates cGMP-dependent protein kinase to mediate VEGF-induced raf-1 and ERK1/2 activation, resulting in VEGF-induced angiogenesis (reviewed by (23)). Our data indicate that eNOS is also a requisite mediator of SDF-1α-induced endothelial cell migration (FIG. 1), yet, the mechanisms whereby eNOS-dependent regulation of SDF-1α signaling in endothelial cell migration occurs is unclear. To determine whether JNK3 and/or ERK1/2 are targets of the NO produced by SDF-1α-induced eNOS activation, L-NMMA was used to inhibit eNOS activation. Interestingly, JNK3 (but not ERK1/2) activation induced by SDF-1α was specifically inhibited by 0.5-5 mM L-NMMA (FIG. 2D), indicating that SDF-1α-induced JNK3 activation is reliant on eNOS-dependent NO generation. To further confirm JNK3 is the target for NO produced by SDF-1α-induced eNOS activation, eNOS siRNAs were transfected into BAECs to knockdown endogenous eNOS protein. As predicted by the previous results (FIG. 2D), JNK3 was activated by SDF-1α in the cells transfected with control siRNA, but it was inhibited in the cells transfected with eNOS siRNA (FIG. 2E). These results support the contention that eNOS is a required mediator for JNK3 activation induced by SDF-1α.

JNKs mediate cell migration through the regulation of focal adhesion assembly, microtubule and actin dynamics (reviewed by Huang (24)). JNK3 has previously been described as a relatively brain-selective JNK iso form and is suggested to be an important therapeutic target for Alzheimer's disease, Parkinson's disease and stroke (reviewed by Resnick (18)). However, the role of JNK3 in endothelial cell migration has not yet been evaluated. Because JNK3 was the only SDF-1α-activated JNK in endothelial cells in our studies (FIG. 2C & FIG. 5, C), we were able to use the general JNK inhibitor SP600125 to test the role of JNK3 in SDF-1α-induced endothelial cell migration. As shown in FIG. 5, D, SP600125 (10 μM or 50 μM) significantly inhibited SDF-1α-mediated endothelial cell migration (from 86±5 cells to 27±3 cells with 10 μM SP600125 or 20±2 cells with 50 μM SP600125, respectively). Interestingly, in the absence of SDF-1α treatment cell migration was also inhibited by SP600125, suggesting that there is a low level of tonic JNK signaling, probably elicited by endogenous SDF. Although ERK activation was not affected by L-NMMA, its inhibition by 20 μM U0126 (an ERK specific inhibitor) also decreased endothelial cell migration induced by SDF-1α (data not shown), which indicates there are both eNOS-dependent and -independent signaling pathways involved in the regulation of SDF-1α-induced cell migration.

Endothelial cell migration is a critical step for tube formation during angiogenesis. To test the importance of JNK3 in highly ordered cell assembly processes, we examined the effect of JNK knockdown with siRNAs on the formation of capillary-like tubes in Matrigel. BAECs were transfected with JNK1 siRNA, JNK2 siRNA, JNK3 siRNA or control siRNA. After 72 hours, cells were plated on Matrigel in medium containing 50 ng/ml SDF-1α. Treatment with SDF-1α significantly enhanced tube formation (FIG. 5, E) with the tube length increasing from 238±136 μm to 605±106 μm. In cells expressing either JNK1 siRNA or JNK2 siRNA tube formation was also increased by SDF-1α from 88±23 μm to 438±108 μm or 121±61 μm to 504±93 μm, respectively (FIG. 2F). In contrast, tube formation was significantly inhibited by ~90.3% in JNK3 siRNA expressing cells. These data once again implicate JNK3 as the critical JNK moiety involved in SDF-1α-dependent angiogenesis.

MKP7 Activity is Inhibited by S-Nitrosylation

The preceding experiments indicate that eNOS and its downstream effector JNK3 are required for SDF-1α-induced endothelial cell migration. However, the molecular mechanisms of eNOS-dependent regulation of JNK3 activity are not intuitive. In the course of exploring various potential regulatory mechanisms, we considered the possibility that regulation of JNK3 by eNOS was determined by suppression of dephosphorylation activities. When cells were incubated with sodium orthovanadate, an inhibitor of protein tyrosine and dual-specificity protein phosphatases, JNK phosphorylation increased both under basal conditions and, most prominently, after SDF-1α treatment (FIG. 3A). These observations suggested to us that JNK phosphatases may be targets for determining JNK3 activation by eNOS. MKP7, a member of the dual-specificity family of protein phosphatases, interacts with the JNK3 scaffold protein β-arrestin2 (25). Located within the N-terminal catalytic domain of MKP7, the $Cys^{244}$ residue is highly sensitive to oxidation due to its low pKa and this oxidation is required for decreased MKP7 activity and sustained activation of JNK3 under certain conditions (26). Given that eNOS is the major source of nitric oxide production in endothelial cells, and in some circumstances can regulate protein function via S-nitrosylation of cysteine residues, we tested: a) if MKP7 could be S-nitrosylated by nitric oxide and b) if S-nitrosylation of MKP7 would affect its ability to regulate JNK3 activity. An in vitro biotin switch nitrosylation assay demonstrated that MKP7 could indeed be S-nitrosylated by the exogenous nitric oxide donor nitrosoglutathione (GSNO) (FIG. 3B). MKP7 S-nitrosylation was also detected with another NO donor-DETA NONOate; the addition of DTT blocked its nitrosylation (data not shown). To further explore the nitrosylation of MKP7 by NO donors, SNOs in MKP7 were replaced with biotin (biotin switch), and peptides generated by trypsinization were purified by avidin chromatography and analyzed by MALDI-TOF and ESI-MS/MS. Several biotinylated cysteine-containing peptides, corresponding to sites of S-nitrosylation, were identified (data not shown), supporting previous results (FIG. 3B) and strongly suggesting that MKP7 can be S-nitrosylated. To determine whether this S-nitrosylation event affected MKP7 activity, we performed an in vitro phosphatase activity analysis using activated JNK3 protein in a reaction with MKP7-concentrated cell lysates. The ectopically-expressed MKP7 protein exhibited strong phosphatase activity as demonstrated by the decrease in JNK3 phosphorylation (FIG. 3C). However, nitrosylation of MKP7 by GSNO markedly inhibited MKP7 phosphatase activity (FIG. 3C). To determine whether $Cys^{244}$ was the targeted residue of MKP7 for this nitrosylation, mutant constructs of MKP7 were generated (FIG. 3D). As shown in FIG. 3E, both MKP7-WT and MKP7-ΔC (A.A.1-317, retaining the catalytic domain) were strongly nitrosylated by GSNO. However, the nitrosylation of MKP7-ΔC ($C^{244}S$) by GSNO was markedly attenuated compared to that of MKP7-ΔC (FIG. 3E). The activities of these mutants were also evaluated using an in vitro phosphatase assay. Both MKP7-WT and MKP7-ΔC possessed strong phosphatase activities as detected by the decreased phosphorylation of JNK3, and their activities decreased dramatically after the treatment of GSNO (FIGS. 3F & G). In contrast, the phosphatase activity of MKP7-ΔC ($C^{244}S$) was much lower than that of MKP7-WT or MKP7-ΔC protein, and the activity after GSNO treatment was essentially unchanged. Collectively, these observations indicate that $Cys^{244}$ located in the catalytic domain of MKP7 is nitrosylated and that S-nitrosylation of the MKP7 protein decreases its activity, providing mechanistic support that MKP7 is the mediator for regulation of JNK3 activity by nitric oxide.

MKP7 S-Nitrosylation Induced by SDF-1α is Required for JNK3 Activation and Cell Migration Since our in vitro data suggested that MKP7 is nitrosylated by nitric oxide and that this nitrosylation inhibits its phosphatase activity, we next tested the relationship between SDF-1α stimulation and MKP7 S-nitrosylation in BAECs. As a first step, we investigated whether SDF-1α treatment of BAECs would result in S-nitrosylation of MKP7. SDF-1α treatment of cells increased MKP7 nitrosylation (FIG. 4A), similar to the dose-dependent increase of MKP7 nitrosylation observed previously with GSNO (data not shown). eNOS siRNA was also utilized to investigate the effect on MKP7 nitrosylation following SDF-1α treatment in BAECs. BAECs were transfected with eNOS siRNA or control siRNA as well as Flag-tagged MKP7. After 72 hours, cells were treated with SDF-1α and a biotin switch assay was performed. Consistent with the result obtained with the eNOS inhibitor L-NMMA (FIG. 4A), eNOS protein knockdown with eNOS siRNA blocked MKP7 nitrosylation following SDF-1α treatment, compared to the cells transfected with control siRNA (FIG. 4B). Next we used JNK3 phosphorylation as a readout for determining whether or not SDF-1α activation of JNK3 could be inhibited by MKP7. Using the MKP7 mutants, we determined that the SDF-1α-induced JNK3 activation was substantially inhibited by MKP7-WT or MKP7-ΔC, but not by MKP7-ΔC ($C^{244}S$) (FIG. 4C). Interestingly, when cells were made to express MKP7-ΔC ($C^{244}S$) to block the endogenous MKP7 phosphatase activity, JNK3 activity increased even under unstimulated conditions (FIG. 4C). Similarly, the mutants of full-length MKP7, MKP7-C244S and MKP7-C244A, failed to decrease JNK3 activity; instead, JNK3 activity increased both under basal and SDF-1α-treated conditions, compared to control cells without SDF-1α treatment (FIG. 4D). These results clearly demonstrate that, following SDF-1α treatment of BAECs, MKP7 is nitrosylated at $Cys^{244}$, and that this event in turn is required for SDF-1α-induced JNK activation. In order to confirm that $Cys^{244}$ in MKP7 is the target of eNOS-induced nitrosylation we repeated the experiment detailed in FIG. 2D, where the eNOS inhibitor LNMMA was used to inhibit SDF-1α-induced JNK3 activation, using MKP7-$C^{244}S$ as a dominant/negative construct. When MKP7-$C^{244}S$ was expressed in the cells, the inhibitory effect of L-NMMA was completely relieved (FIG. 4E). This result strongly implies that endogenous MKP7 is the mediator for eNOS-dependent JNK3 activation. Together with the data presented previously that overexpressed MKP7 could be nitrosylated by nitric oxide and eNOS siRNA inhibited its nitrosylation, it supported that endogenous MKP7 could be nitrosylated by nitric oxide generated by active eNOS, which in turn regulates JNK3 activity.

To ascertain the functional consequences of MKP7 S-nitrosylation, we performed endothelial cell migration assays using the various MKP7 mutants. As shown in FIG. 4F, SDF-1α treatment increased endothelial cell migration from 38±7 to 125±9 cells/field. Expression of MKP7-WT or MKP7-ΔC in BAECs significantly decreased cell migration from 125±9 to 84±12 or 53±2 cells per field, respectively, however SDF-1α-induced cell migration was not inhibited by MKP7-ΔC ($C^{244}S$) (from 125±9 to 109±14 cells per field). Although cells transfected with MKP7-ΔC ($C^{244}S$) exhibited higher JNK3 activity under basal conditions (FIG. 4C), cell migration was not increased (FIG. 4F), suggesting that JNK3 activity is required but probably not sufficient for SDF-1α-induced cell migration and that other mediators responsive to SDF-1α, such as ERK1/2, may also be required for the highly coordinated process of cell migration. Collectively, these data indicate that MKP7 nitrosylation by nitric oxide following SDF-1α-induced eNOS activation provides a critical checkpoint for JNK3 activation and subsequent endothelial cell migration following SDF-1α treatment. Furthermore, these studies articulate a mechanism through which MKP7 is a key participant in the coordination of events mediated by eNOS and JNK3 after activation by SDF-1α.

Discussion

The major finding of this study is the discovery that SDF-1α activates JNK3 in endothelial cells and that this activation is required for SDF-1α-induced endothelial cell migration. In addition, we demonstrate that JNK3 activation is eNOS-dependent. Specifically, MKP7—a JNK3 phosphatase—can be nitrosylated and inhibited by nitric oxide following SDF-1α-induced eNOS activation. The inhibition of MKP7 activity by SDF-1α treatment is critical for JNK3 activation and the resultant endothelial migration. These observations reinforce the importance of nitric oxide and S-nitrosylation in cell migration and angiogenesis. In addition, the findings provide mechanistic insight into the signaling pathways responsible for SDF-1α-induced JNK3 activation of endothelial cells, strongly suggesting the need for crosstalk between eNOS and MAP kinases through the 'bridge' molecule-MKP7. The critical roles of MKP7 and JNK3 in SDF-1α-induced cell migration provide novel and unexpected therapeutic targets for angiogenesis-related diseases.

SDF-1α and its receptor CXCR4 are considered to be critical for endothelial migration and in vivo neovascularization (5, 15, 16). SDF-1α activates Akt/eNOS and MAP kinases including ERK1/2 and p38 in different cell types (including endothelial cells and EPCs), resulting in a vast array of consequences including cell migration, apoptosis and cell survival (27-30). However, until now no detailed description of the signaling pathways involved in SDF-1α-dependent angiogenesis have been published. Likewise, although eNOS and its generated nitric oxide have long been considered critical for SDF-1α-mediated endothelial cell migration and angiogenesis, the exact mechanisms by which eNOS regulates SDF-1α-dependent endothelial cell migration have until now been a mystery. Our results demonstrate that JNK3, but not the other MAP kinases ERK1/2 or p38, acts downstream of eNOS to promote endothelial cell migration. This discovery increases our understanding of the role that eNOS and nitric oxide play in SDF-1α-induced endothelial activation. However, this JNK3/eNOS-dependent pathway is not the only SDF-1α-induced migration mechanism employed by endothelial cells. Our results also point to an eNOS-independent pathway for MAP kinase-associated cell migration mediated by ERK1/2 and p38. ERK1/2 but not p38 was significantly activated by SDF in BAECs (FIGS. 2, A & B, and data not shown). It has been shown that SDF-1α can activate p38 in other cultured cell types (28), but we did not detect p38 activation by SDF-1α, suggesting cellular specificity in the regulation of p38 by SDF-1α. The requirement of both eNOS-dependent and independent MAP kinase activation pathways for endothelial cell migration is consistent with the complex nature of cellular migration and angiogenesis in general. The eNOS-dependent and independent pathways coordinating the migratory responses of endothelial cells in response to SDF-1α are an avenue of further investigation.

S-nitrosylation of proteins by nitric oxide is one of the major avenues of nitric oxide regulation of multiple cellular responses, including DNA repair, host defense, blood pressure control and neurotransmission (31). More than 100 proteins have been reported to be S-nitrosylated in cells including JNK1 and JNK3, resulting in either inhibition or activation of protein function (32). JNK1 activity is suppressed following nitrosylation on Cys116 of JNK1 by nitric oxide generated after IFN-γ administration in macrophages (33). Conversely, nitric oxide mediates ERK and JNK activation during hypoxia in neuronal cells (34) and increases nitrosylation and phosphorylation of JNK3 in hippocampal CA1 cells (35). In our study, JNK3 activity was positively regulated by S-nitrosylation, although the target of this S-nitrosylation appears to be the JNK3 phosphatase-MKP7 and not JNK3 directly (FIG. 3). The inhibitory effect of NMMA was relieved by expression of the dominant negative form of MKP7 (FIG. 4E) strongly suggests that JNK3 or its upstream kinases are not the dominant targets of eNOS and nitrosylation.

EPCs, improving neovascularization, are increasingly considered as therapeutic tools for the prevention of vascular diseases, and gene-targeted endothelial progenitor cells are considered potential carriers of targeted therapies for cancers (36). SDF-1α is known to be a key player in EPC mobilization and homing processes in animal models, similar to other cytokines such as granulocyte-colony stimulating factor, granulocyte monocyte-colony stimulating factor and VEGF165 (38). Although future experiments are still needed in order to determine if eNOS and JNK3 contribute coordinately to EPC-mediated neovascularization, this study provides insights into the signaling pathways responsible for SDF-1α-dependent angiogenesis and shed more light on the therapeutic options for cell-based neovascularization therapies against vascular diseases, stroke and cancer.

Example 2

JNK3 is Required for Oxygen-Induced Retinal Neovascularization In Vivo

In vitro data suggested that JNK3 is critical for SDF1α-induced endothelial migration and angiogenesis. Therefore, JNK3 was tested to determine if it is important for angiogenesis in vivo. There are no apparent defects in developmental vascular pattern formation in JNK3 knockout mice. Since SDF1α is one of the major pro-angiogenic factors in diabetic retinopathy, the role of JNK3 in physiological and pathological retinal vessel formation was studied with JNK3 knockout mice. The first experiment was to evaluate the development of retinal vasculature in JNK3$^{-/-}$ mice. There was no significant change in the retinal vessel formation after the measurement of primary vascular network area by flat-mount isolectin staining in the retina at postnatal day P6 and P12, with similar vascular area in JNK3$^{-/-}$ and JNK3$^{+/+}$ mice (FIG. 6A). JNK3$^{+/+}$ or JNK3$^{-/-}$ mice were then studied with oxygen-induced neovascularization model. Specifically, postnatal day P7 mice were placed in constant 75% $O_2$ for five days to induce retinal capillary obliteration centrally. After hyperoxia, mice were placed into room air (the relatively hypoxic condition) to permit retinal neovascularization. There were markedly decreased neovascularization, demonstrated as the increase in avascular area, in JNK3$^{-/-}$ mice flowing hypoxic injury for 1 day (P13) or 3 days (P15) (FIG. 6B). This data suggests that JNK3 is required for oxygen-induced retinal neovascularization. It also provides further in vivo evidence for JNK3 as a potential therapeutic target for angiogenesis-dependent diseases.

REFERENCES

1. Horuk, R. (2001) Chemokine receptors *Cytokine & growth factor reviews* 12: 313-335.
2. Dias, S., Choy, M., & Rafii, S. (2001) The role of CXC chemokines in the regulation of tumor angiogenesis *Cancer investigation* 19: 732-738.
3. Pourtau, J., Mirshahi, F., Li, H., Muraine, M., Vincent, L., Tedgui, A., Vannier, J. P., Soria, J., Vasse, M., & Soria, C. (1999) Cyclooxygenase-2 activity is necessary for the angiogenic properties of oncostatin M *FEBS letters* 459: 453-457.
4. Molino, M., Woolkalis, M. J., Prevost, N., Pratico, D., Barnathan, E. S., Taraboletti, G., Haggarty, B. S., Hesselgesser, J., Horuk, R., Hoxie, J. A., et al. (2000) CXCR4 on human endothelial cells can serve as both a mediator of biological responses and as a receptor for HIV-2 *Biochimica et biophysica acta* 1500: 227-240.
5. Mirshahi, F., Pourtau, J., Li, H., Muraine, M., Trochon, V., Legrand, E., Vannier, J., Soria, J., Vasse, M., & Soria, C. (2000) SDF-1 activity on microvascular endothelial cells: consequences on angiogenesis in in vitro and in vivo models *Thrombosis research* 99: 587-594.
6. Askari, A. T., Unzek, S., Popovic, Z. B., Goldman, C. K., Forudi, F., Kiedrowski, M., Rovner, A., Ellis, S. G., Thomas, J. D., DiCorleto, P. E., et al. (2003) Effect of stromal cell-derived factor 1 on stem-cell homing and tissue regeneration in ischaemic cardiomyopathy *Lancet* 362: 697-703.
7. Yamaguchi, J., Kusano, K. F., Masuo, O., Kawamoto, A., Silver, M., Murasawa, S., Bosch-Marce, M., Masuda, H., Losordo, D. W., Isner, J. M., et al. (2003) Stromal cell derived factor-1 effects on ex vivo expanded endothelial progenitor cell recruitment for ischemic neovascularization *Circulation* 107: 1322-1328.
8. Ceradini, D. J., Kulkarni, A. R., Callaghan, M. J., Tepper, O. M., Bastidas, N., Kleinman, M. E., Capla, J. M., Galiano, R. D., Levine, J. P., & Gurtner, G. C. (2004) Progenitor cell trafficking is regulated by hypoxic gradients through HIF-1 induction of SDF-1 *Nature medicine* 10: 858-864.
9. Zou, Y. R., Kottmann, A. H., Kuroda, M., Taniuchi, I., & Littman, D. R. (1998) Function of the chemokine receptor CXCR4 in haematopoiesis and in cerebellar development *Nature* 393: 595-599.
10. Ma, Q., Jones, D., Borghesani, P. R., Segal, R. A., Nagasawa, T., Kishimoto, T., Bronson, R. T., & Springer, T. A. (1998) Impaired B-lymphopoiesis, myelopoiesis, and derailed cerebellar neuron migration in CXCR4- and SDF-1-deficient mice *Proc Natl Acad Sci USA* 95: 9448-9453.
11. Bagri, A., Gurney, T., He, X., Zou, Y. R., Littman, D. R., Tessier-Lavigne, M., & Pleasure, S. J. (2002) The chemokine SDF1 regulates migration of dentate granule cells *Development* 129: 4249-4260.
12. Lu, M., Grove, E. A., & Miller, R. J. (2002) Abnormal development of the hippocampal dentate gyrus in mice lacking the CXCR4 chemokine receptor *Proc Natl Acad Sci USA* 99: 7090-7095.
13. Nagasawa, T., Hirota, S., Tachibana, K., Takakura, N., Nishikawa, S., Kitamura, Y., Yoshida, N., Kikutani, H., & Kishimoto, T. (1996) Defects of B-cell lymphopoiesis and bone-marrow myelopoiesis in mice lacking the CXC chemokine PBSF/SDF-1 *Nature* 382: 635-638.

14. Tachibana, K., Hirota, S., Iizasa, H., Yoshida, H., Kawabata, K., Kataoka, Y., Kitamura, Y., Matsushima, K., Yoshida, N., Nishikawa, S., et al. (1998) The chemokine receptor CXCR4 is essential for vascularization of the gastrointestinal tract *Nature* 393: 591-594.
15. Gupta, S. K., Lysko, P. G., Pillarisetti, K., Ohlstein, E., & Stadel, J. M. (1998) Chemokine receptors in human endothelial cells. Functional expression of CXCR4 and its transcriptional regulation by inflammatory cytokines *J Biol Chem* 273: 4282-4287.
16. Salcedo, R., Wasserman, K., Young, H. A., Grimm, M. C., Howard, O. M., Anver, M. R., Kleinman, H. K., Murphy, W. J., & Oppenheim, J. J. (1999) Vascular endothelial growth factor and basic fibroblast growth factor induce expression of CXCR4 on human endothelial cells: In vivo neovascularization induced by stromal-derived factor-1alpha *The American journal of pathology* 154: 1125-1135.
17. Zheng, H., Fu, G., Dai, T., & Huang, H. (2007) Migration of endothelial progenitor cells mediated by stromal cell-derived factor-1alpha/CXCR4 via PI3K/Akt/eNOS signal transduction pathway *Journal of cardiovascular pharmacology* 50: 274-280.
18. Resnick, L. & Fennell, M. (2004) Targeting JNK3 for the treatment of neurodegenerative disorders *Drug discovery today* 9: 932-939.
19. Pi, X., Ren, R., Kelley, R., Zhang, C., Moser, M., Bohil, A. B., Divito, M., Cheney, R. E., & Patterson, C. (2007) Sequential roles for myosin-X in BMP6-dependent filopodial extension, migration, and activation of BMP receptors *J Cell Biol* 179: 1569-1582.
20. Hatano, N., Mori, Y., Oh-hora, M., Kosugi, A., Fujikawa, T., Nakai, N., Niwa, H., Miyazaki, J., Hamaoka, T., & Ogata, M. (2003) Essential role for ERK2 mitogen activated protein kinase in placental development *Genes Cells* 8: 847-856.
21. Mudgett, J. S., Ding, J., Guh-Siesel, L., Chartrain, N. A., Yang, L., Gopal, S., & Shen, M. M. (2000) Essential role for p38alpha mitogen-activated protein kinase in placental angiogenesis *Proc Natl Acad Sci USA* 97: 10454-10459.
22. Hu, X., Dai, S., Wu, W. J., Tan, W., Zhu, X., Mu, J., Guo, Y., Bolli, R., & Rokosh, G. (2007) Stromal cell derived factor-1 alpha confers protection against myocardial ischemia/reperfusion injury: role of the cardiac stromal cell derived factor-1 alpha CXCR4 axis *Circulation* 116: 654-663.
23. Ziche, M. & Morbidelli, L. (2000) Nitric oxide and angiogenesis *J Neurooncol* 50: 139-148.
24. Huang, C., Jacobson, K., & Schaller, M. D. (2004) MAP kinases and cell migration *J Cell Sci* 117: 4619-4628.
25. Willoughby, E. A. & Collins, M. K. (2005) Dynamic interaction between the dual specificity phosphatase MKP7 and the JNK3 scaffold protein beta-arrestin 2 *J Biol Chem* 280: 25651-25658.
26. Kamata, H., Honda, S., Maeda, S., Chang, L., Hirata, H., & Karin, M. (2005) Reactive oxygen species promote TNFalpha-induced death and sustained JNK activation by inhibiting MAP kinase phosphatases *Cell* 120: 649-661.
27. Cherla, R. P. & Ganju, R. K. (2001) Stromal cell-derived factor 1 alpha-induced chemotaxis in T cells is mediated by nitric oxide signaling pathways *J Immunol* 166: 3067-3074.
28. Sun, Y., Cheng, Z., Ma, L., & Pei, G. (2002) Beta-arrestin2 is critically involved in CXCR4-mediated chemotaxis, and this is mediated by its enhancement of p38 MAPK activation *J Biol Chem* 277: 49212-49219.
29. Kaminski, A., Ma, N., Donndorf, P., Lindenblatt, N., Feldmeier, G., Ong, L., Furlani, D., Skrabal, C., Liebold, A., Vollmar, B., & Steinhoff, G. (2008) Endothelial NOS is required for SDF-1/CXCR4-mediated peripheral endothelial adhesion of c-kit+ bone marrow stem cells *Lab Invest* 88:58-69.
30. Hiasa, K., Ishibashi, M., Ohtani, K., Inoue, S., Zhao, Q., Kitamoto, S., Sata, M., Ichiki, T., Takeshita, A., Egashira, K. (2004) Gene Transfer of Stromal Cell-Derived Factor-1 Enhances Ischemic Vasculogenesis and Angiogenesis via Vascular Endothelial Growth Factor/Endothelial Nitric Oxide Synthase-Related Pathway *Circulation* 109:2454-2461.
31. Stamler, J. S. (1994) Redox signaling: nitrosylation and related target interactions of nitric oxide *Cell* 78: 931-936.
32. Hess, D. T., Matsumoto, A., Kim, S. O., Marshall, H. E., & Stamler, J. S. (2005) Protein S-nitrosylation: purview and parameters *Nat Rev Mol Cell Biol* 6: 150-166.
33. Park, H. S., Huh, S. H., Kim, M. S., Lee, S. H., & Choi, E. J. (2000) Nitric oxide negatively regulates c-Jun N-terminal kinase/stress-activated protein kinase by means of S-nitrosylation *Proc Natl Acad Sci USA* 97: 14382-14387.
34. Mishra, O. P., Zubrow, A. B., & Ashraf, Q. M. (2004) Nitric oxide-mediated activation of extracellular signal-regulated kinase (ERK) and c-jun N-terminal kinase (JNK) during hypoxia in cerebral cortical nuclei of newborn piglets *Neuroscience* 123: 179-186.
35. Pei, D. S., Song, Y. J., Yu, H. M., Hu, W. W., Du, Y., & Zhang, G. Y. (2008) Exogenous nitric oxide negatively regulates c-Jun N-terminal kinase activation via inhibiting endogenous NO-induced S-nitrosylation during cerebral ischemia and reperfusion in rat hippocampus *Journal of neurochemistry* 106: 1952-1963.
36. Isner, J. M. & Asahara, T. (1999) Angiogenesis and vasculogenesis as therapeutic strategies for postnatal neovascularization *The Journal of clinical investigation* 103: 1231-1236.
37. Urbich, C. & Dimmeler, S. (2004) Endothelial progenitor cells: characterization and role in vascular biology *Circ Res* 95: 343-353.
38. Moore, M. A., Hattori, K., Heissig, B., Shieh, J. H., Dias, S., Crystal, R. G., & Rafii, S. (2001) Mobilization of endothelial and hematopoietic stem and progenitor cells by adenovector-mediated elevation of serum levels of SDF-1, VEGF, and angiopoietin-1 *Annals of the New York Academy of Sciences* 938: 36-45; discussion 45-37.
39. Forrester, M. T., Foster, M. W., & Stamler, J. S. (2007) Assessment and application of the biotin switch technique for examining protein S-nitrosylation under conditions of pharmacologically induced oxidative stress *J Biol Chem* 282: 13977-13983.
40. Pi, X., Garin, G., Xie, L., Zheng, Q., Wei, H., Abe, J., Yan, C., & Berk, B. C. (2005) BMK1/ERK5 is a novel regulator of angiogenesis by destabilizing hypoxia inducible factor 1alpha *Circ Res* 96: 1145-1151.
41. Ren, R., Charles, P. C., Zhang, C., Wu, Y., Wang, H., & Patterson, C. (2006) Gene expression profiles identify a role for cyclooxygenase 2-dependent prostanoid generation in BMP6-induced angiogenic responses *Blood* 109: 2847-2853

All publications and patent applications mentioned in the specification are indicative of the level of skill of those skilled in the art to which this invention pertains.

All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of inhibiting JNK3 mediated endothelial cell migration or proliferation in a subject in need thereof, comprising administering to said subject an effective amount of at least one JNK3-specific inhibitor, wherein said JNK3-specific inhibitor directly inhibits JNK3 and is an organic or inorganic molecule.

2. The method of claim 1 wherein said JNK3-specific inhibitor reduces or inhibits endothelial tube formation.

3. The method of claim 1 wherein said JNK3-specific inhibitor reduces or inhibits wound healing.

4. The method of claim 1 wherein said JNK3-specific inhibitor reduces or inhibits neovascularization.

5. The method of claim 1 wherein said JNK3-specific inhibitor is the molecule SP600125.

* * * * *

UNITED STATES PATENT AND TRADEMARK OFFICE
CERTIFICATE OF CORRECTION

| | | |
|---|---|---|
| PATENT NO. | : 8,153,589 B2 | Page 1 of 1 |
| APPLICATION NO. | : 12/764356 | |
| DATED | : April 10, 2012 | |
| INVENTOR(S) | : Patterson et al. | |

It is certified that error appears in the above-identified patent and that said Letters Patent is hereby corrected as shown below:

Column 1, lines 15-19, delete entire paragraph and replace with the following paragraph:
--This invention was made with government support under Grant Nos. HL003658, HL061656 and HL072347 awarded by the National Institutes of Health. The government has certain rights in this invention.--

Signed and Sealed this
Twenty-ninth Day of May, 2012

David J. Kappos
*Director of the United States Patent and Trademark Office*

SEQUENCE LISTING

<160> NUMBER OF SEQ ID NOS: 9

<210> SEQ ID NO 1
<211> LENGTH: 25
<212> TYPE: RNA
<213> ORGANISM: Artificial Sequence
<220> FEATURE:
<223> OTHER INFORMATION: eNOS siRNA1

<400> SEQUENCE: 1
cggugaagau cucugccuca cucau                                                25

<210> SEQ ID NO 2
<211> LENGTH: 25
<212> TYPE: RNA
<213> ORGANISM: Artificial Sequence
<220> FEATURE:
<223> OTHER INFORMATION: eNOS siRNA2

<400> SEQUENCE: 2
uguugcugga cuccuuucuc uuccg                                                25

<210> SEQ ID NO 3
<211> LENGTH: 25
<212> TYPE: RNA
<213> ORGANISM: Artificial Sequence
<220> FEATURE:
<223> OTHER INFORMATION: eNOS siRNA3

<400> SEQUENCE: 3
uacguauacg gcuugucacc uccug                                                25

<210> SEQ ID NO 4
<211> LENGTH: 25
<212> TYPE: RNA
<213> ORGANISM: Artificial Sequence
<220> FEATURE:
<223> OTHER INFORMATION: JNK1 siRNA

<400> SEQUENCE: 4
auaacaaauc ccuugccuga cuggc                                                25

<210> SEQ ID NO 5
<211> LENGTH: 25
<212> TYPE: RNA
<213> ORGANISM: Artificial Sequence
<220> FEATURE:
<223> OTHER INFORMATION: JNK2 siRNA

<400> SEQUENCE: 5
aguugagucu gccacuugua cacug                                                25

<210> SEQ ID NO 6
<211> LENGTH: 25
<212> TYPE: RNA
<213> ORGANISM: Artificial Sequence
<220> FEATURE:
<223> OTHER INFORMATION: JNK3 siRNA

<400> SEQUENCE: 6
gauauauggu cugugggaug cauua                                                25

<210> SEQ ID NO 7
<211> LENGTH: 25
<212> TYPE: RNA

```
<213> ORGANISM: Artificial Sequence
<220> FEATURE:
<223> OTHER INFORMATION: JNK3 siRNA

<400> SEQUENCE: 7
cacuggagga guuccaagau guuua                                      25

<210> SEQ ID NO 8
<211> LENGTH: 25
<212> TYPE: RNA
<213> ORGANISM: Artificial Sequence
<220> FEATURE:
<223> OTHER INFORMATION: JNK3 siRNA

<400> SEQUENCE: 8
uagcaucuuu gacagcaagu cucug                                      25

<210> SEQ ID NO 9
<211> LENGTH: 25
<212> TYPE: RNA
<213> ORGANISM: Artificial Sequence
<220> FEATURE:
<223> OTHER INFORMATION: control siRNA

<400> SEQUENCE: 9
cgggaacuac aagacacgug cugaa                                      25
```